(12) United States Patent
Stoy et al.

(10) Patent No.: US 10,667,903 B2
(45) Date of Patent: Jun. 2, 2020

(54) BIOANALOGIC INTRAOCULAR LENS

(71) Applicant: Medicem Ophthalmic (CY) Limited, Limassol (CY)

(72) Inventors: Vladimir Stoy, Tuchomerice (CZ); Eugen Chicevic, Prague (CZ)

(73) Assignee: MEDICEM INSTITUTE S.R.O., Kamenne Zehrovice (CZ)

(*) Notice: Subject to any disclaimer, the term of this patent is extended or adjusted under 35 U.S.C. 154(b) by 0 days.

(21) Appl. No.: 14/760,868

(22) PCT Filed: Dec. 12, 2013

(86) PCT No.: PCT/IB2013/060869
§ 371 (c)(1),
(2) Date: Jul. 14, 2015

(87) PCT Pub. No.: WO2014/111769
PCT Pub. Date: Jul. 24, 2014

(65) Prior Publication Data
US 2015/0351901 A1    Dec. 10, 2015

Related U.S. Application Data

(60) Provisional application No. 61/752,685, filed on Jan. 15, 2013.

(51) Int. Cl.
*A61F 2/16*    (2006.01)

(52) U.S. Cl.
CPC .......... *A61F 2/1648* (2013.01); *A61F 2/1613* (2013.01); *A61F 2230/0063* (2013.01); *A61F 2230/0067* (2013.01)

(58) Field of Classification Search
CPC ...... A61F 2/1637; A61F 2/164; A61F 2/1643; A61F 2/1645; A61F 2/1648; A61F 2002/169
See application file for complete search history.

(56) References Cited

U.S. PATENT DOCUMENTS 4,562,600 A * 1/1986 Ginsberg .................. A61F 2/16
                                                                623/6.15
4,731,078 A * 3/1988 Stoy ...................... A61F 2/1648
                                                                623/6.13
(Continued)

FOREIGN PATENT DOCUMENTS

CN        101027014 A    8/2007
CN        101522133 A    9/2009
(Continued)

OTHER PUBLICATIONS

Bille et al., "Chemical basis for alteration of an intraocular lens using femtosecond laser," Biomedical Optics Express (Mar. 1, 2017); 8(3):1390-1404.
(Continued)

*Primary Examiner* — Leslie Lopez
(74) *Attorney, Agent, or Firm* — Fox Rothschild LLP

(57) ABSTRACT

A bioanalogic implantable ophthalmic lens ("BIOL") capable of replacing the natural crystalline lens (NCL) in its various essential functions after the NCL having been removed and BIOL implanted into the posterior eye chamber and placed into the capsular bag vacated from the NCL. At least the posterior surface of the lens has a convex shape and is made from a transparent flexible hydrogel material. At least the anterior and posterior optical surfaces are defined by rotation of one or more conic sections along the main optical axis and the surfaces defined by the rotation will include a plane perpendicular to the axis and conical surface symmetrical by the axis.

23 Claims, 12 Drawing Sheets

(56) References Cited

U.S. PATENT DOCUMENTS

| | | | |
|---|---|---|---|
| 5,310,779 A | 5/1994 | Lai | |
| 5,674,283 A * | 10/1997 | Stoy | A61F 2/1616 264/1.1 |
| 6,190,410 B1 | 2/2001 | Lamielle et al. | |
| 6,244,707 B1 | 6/2001 | Faubl | |
| 6,329,485 B1 | 12/2001 | Vanderbilt | |
| 7,789,910 B2 | 9/2010 | Knox et al. | |
| 8,292,952 B2 | 10/2012 | Bille | |
| 8,337,553 B2 | 12/2012 | Knox et al. | |
| 8,568,627 B2 | 10/2013 | Bille | |
| 8,901,190 B2 | 12/2014 | Smith et al. | |
| 8,920,690 B2 | 12/2014 | Bille | |
| 8,932,352 B2 | 1/2015 | Knox et al. | |
| 9,023,257 B2 | 5/2015 | Sahler et al. | |
| 9,060,847 B2 | 6/2015 | Smith et al. | |
| 9,107,746 B2 | 8/2015 | Sahler et al. | |
| 9,186,242 B2 | 11/2015 | Sahler et al. | |
| 9,192,292 B2 | 11/2015 | Bille | |
| 9,622,912 B2 | 4/2017 | Knox et al. | |
| 2003/0055499 A1 | 3/2003 | Nguyen et al. | |
| 2003/0097177 A1 | 5/2003 | Tran | |
| 2003/0129223 A1 * | 7/2003 | Wartchow | A61K 49/0002 424/450 |
| 2004/0252274 A1 * | 12/2004 | Morris | G02C 7/044 351/159.44 |
| 2006/0004163 A1 | 1/2006 | Makker et al. | |
| 2006/0142528 A1 | 6/2006 | Jethmalani et al. | |
| 2006/0244904 A1 | 11/2006 | Hong et al. | |
| 2007/0242215 A1 * | 10/2007 | Schorzman | C08F 230/08 351/159.01 |
| 2008/0001320 A1 | 1/2008 | Knox et al. | |
| 2009/0224415 A1 * | 9/2009 | Michalek | B29C 41/04 264/1.36 |
| 2010/0228345 A1 | 9/2010 | Bille | |
| 2013/0178934 A1 | 7/2013 | Knox et al. | |
| 2016/0074967 A1 | 3/2016 | Sahler et al. | |
| 2017/0181846 A1 | 6/2017 | Knox et al. | |

FOREIGN PATENT DOCUMENTS

| | | |
|---|---|---|
| CN | 101547662 A | 9/2009 |
| CN | 101636127 A | 1/2010 |
| CN | 101641060 A | 2/2010 |
| GB | 2151371 A | 7/1985 |
| JP | 3284258 B2 | 5/2002 |
| JP | 2008520310 A | 6/2008 |
| WO | 00008516 A1 | 2/2000 |
| WO | 2006054178 A2 | 5/2006 |
| WO | 06060971 A1 | 6/2006 |
| WO | 2012016096 A1 | 2/2012 |
| WO | 2014/111769 A1 | 7/2014 |

OTHER PUBLICATIONS

Dubbleman et al., "The shape of the aging human lens: curature, equivalent refractive index and the lens paradox," Vision Research (2001); 41:1867-1877.

* cited by examiner

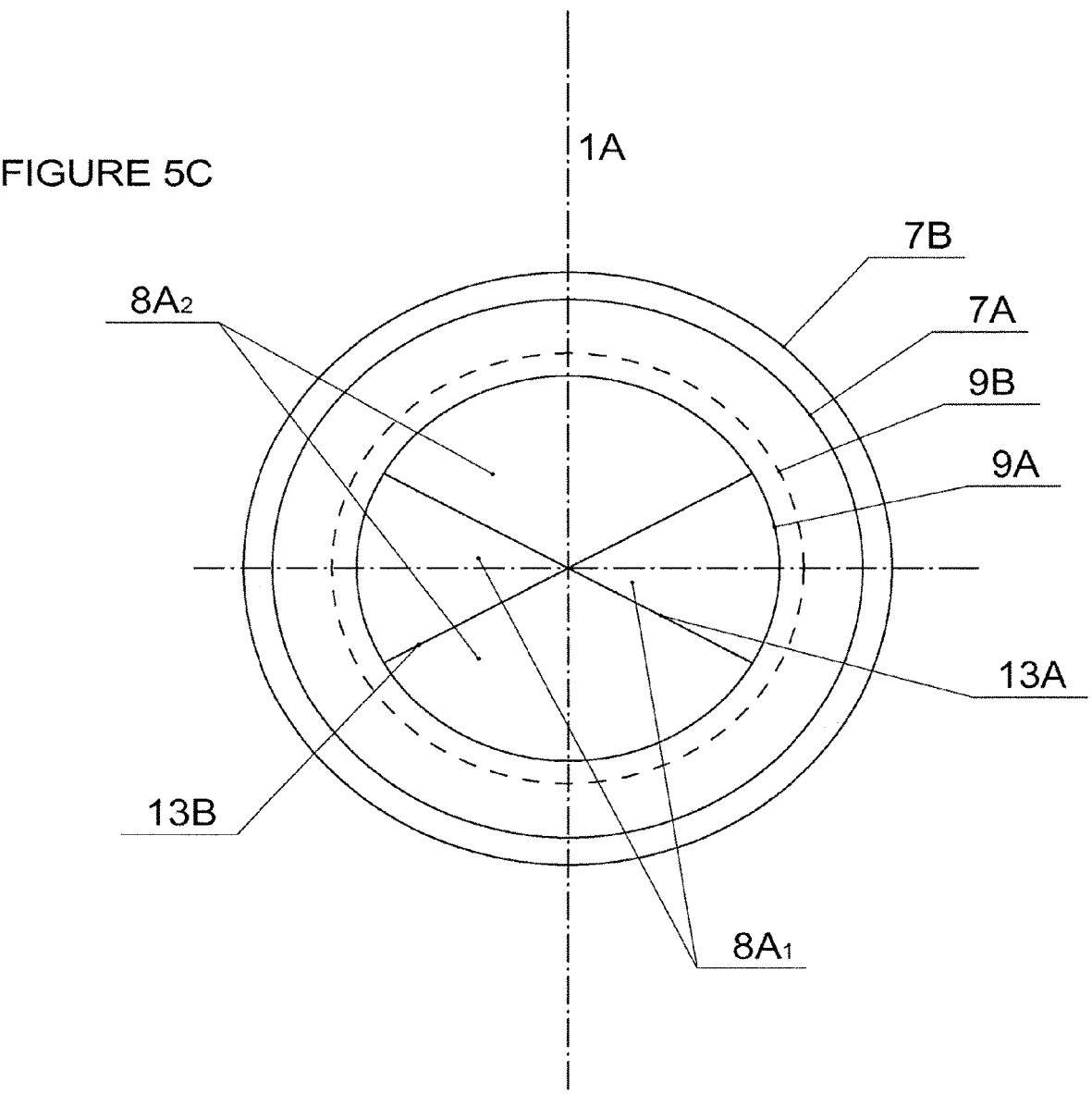

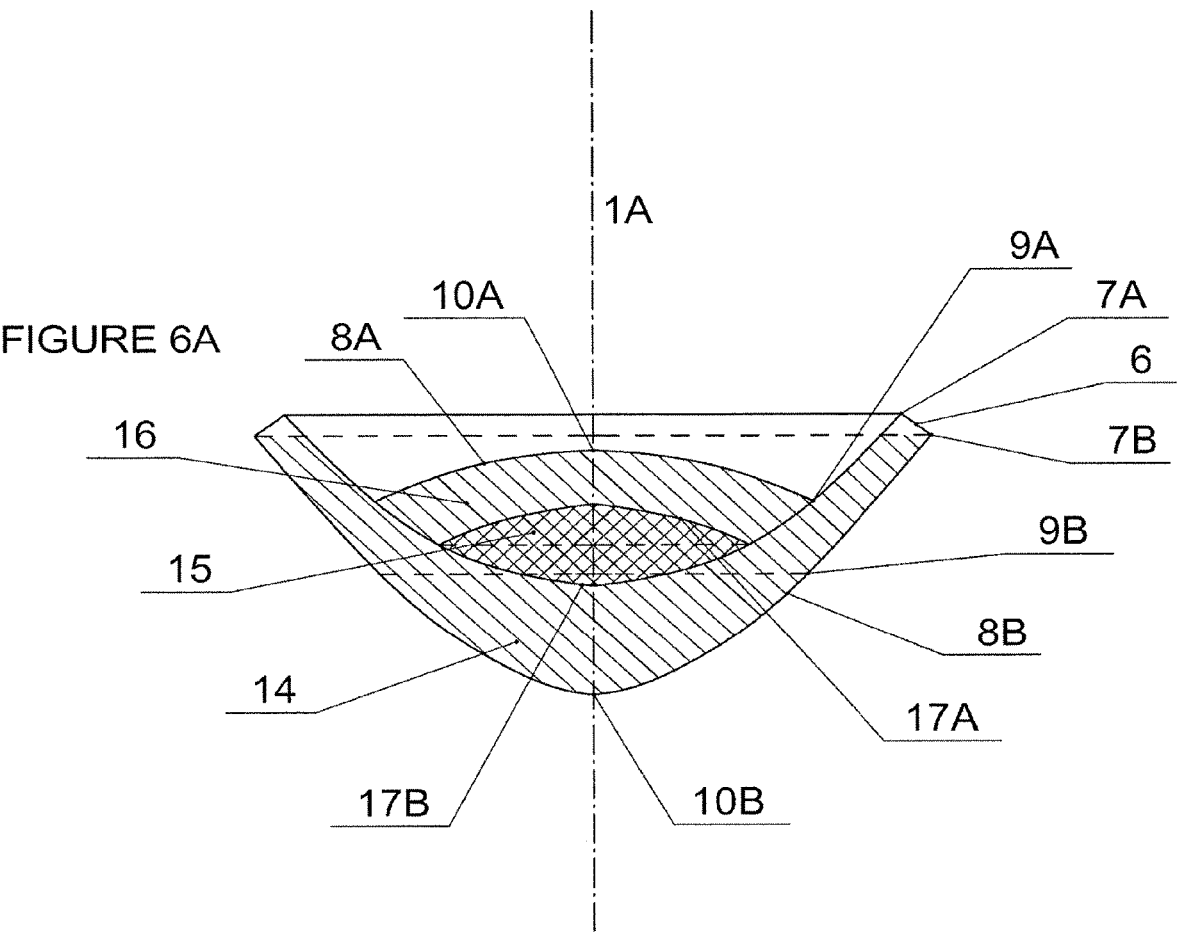

BIOANALOGIC INTRAOCULAR LENS

This application is a U.S. National Phase of International Application No. PCT/IB/2013/060869, which claims the benefit of U.S. Provisional Application No. 61/752,685, filed on Jan. 15, 2013, the contents of which are incorporated herein by reference.

FIELD OF THE INVENTION

This invention relates to a bioanalogic implantable ophthalmic lens ("BIOL") capable of replacing the natural crystalline lens (NCL) in its various essential functions after the NCL has been removed and the BIOL implanted into the posterior eye chamber and placed into the capsular bag vacated by the NCL.

BACKGROUND OF THE INVENTION

Intra ocular lenses (IOLs) are surgically implantable lenses which replace or supplement optical function of the NCL. So called "posterior chamber intraocular lens", or PC IOLs, replace the NCL in the case of cataract or, more recently, in the case of presbyopia by so called "clear lens exchange", or CLE. Other implantable lenses are placed into the anterior chamber of the eye (AC IOLs), into the cornea (corneal or intrastromal implants) or between the NCL and iris (so called "implantable contact lens" or ICL). So far, most of these IOLs were designed to replace or to supplement the basic optical function of the NCL only. It should be appreciated that an NCL in a human eye, depicted in the FIG. 1, is a complicated structure with several functions. The main eye parts include the cornea 101; the iris 102; the NCL 103; the posterior capsule 104; the cilliary muscle 105; the zonules 106; the vitreous body 107; and the retina 108.

The basic optical function of the NCL 103 consists in helping the cornea 101 to focus the incoming light so that a distant object can be projected on the retina 108. The other important optical function is accommodation—adjustment of optical power of the lens in such a way that objects at various distances can be projected onto the retina 108. There are several theories explaining the accommodation mechanism. See for example L. Werner et al, Physiology of Accommodation and Presbyopia, ARQ. BRAS. OFTALMOL. 63(6), DEZEMBRO/2000-503.

The most firmly established theory is von Helmholtz theory explaining that, referring to the FIG. 1, relaxed cilliary muscle 105 causes tension in the zonules 106 that pull the lens 103 periphery outward to keep the NCL 103 in its deformed (flattened) shape that provides a lower refractive power suitable for distant vision. Focusing on a near object is caused by tension in the cilliary muscle 105 that relaxes the zonules 106 and allows the NCL 103 to obtain its "natural" configuration with a smaller diameter, larger central thickness and smaller radii of curvature on both anterior and posterior surfaces. This increases the NCL's refractive power and allows for projection of the image of near objects on the retina 108.

Most of the common intraocular lenses have spherical surfaces that can be manufactured rather readily. It has been assumed for some time that the NCL 103 is essentially spherical. However, a spherical lens is not exactly monofocal, instead it demonstrates so called "spherical aberration" wherein rays incoming through the center are bent into a focal point that is slightly further from the lens than rays incoming through the lens periphery. Therefore, a spherical lens is somewhat more refractive in its periphery than in its center. This change is continuous: such a lens does not have a single focal point, but many focal points in a short interval of distances (focal range) between the longest and shortest focal distance. In other words, a spherical lens is negatively polyfocal (its focal distance decreases from the center to the periphery). Lenses with elliptical rather than spherical surfaces (such as surfaces created by solidification of a static liquid meniscus) have even more distinct spherical aberration and are, therefore, even more negatively polyfocal than spherical lens.

Some artificial intraocular lenses include hyperbolic surfaces alongside with other surfaces of second order, such as spheric or even elliptic surfaces that have negative polyfocality and very opposite optical effect. More importantly, the prior art generally combines second order (or conic section) surfaces with meniscoid surfaces that are poorly defined and merely approximate second order surfaces with positive spherical aberration (although never surfaces with hyperbolic aberration).

For example, Wichterle in U.S. Pat. No. 4,971,732 claims the meniscoid surfaces to approximate a flat ellipsoid while Stoy in U.S. Pat. No. 5,674,283 considers meniscoid surfaces an approximation of a spherical surface, both having negative polyfocality. A combination of surfaces with positive and negative polyfocality diminishes or negates advantages of the former.

Furthermore, Wichterle '732 describes a manufacturing method of the intraocular lens where a monomer solidifies in an open mold, one (posterior) side of the lens having the shape of the mold cavity while the anterior side has a shape of a solidified liquid meniscus (presumably approximating a flat ellipsoid shape with negative polyfocality, being somewhere between purely spherical and purely ellipsoid surface). The mold cavity has the shape of a second order surface that may include a hyperbolic surface. One can note that each of the optical surfaces is created differently—one by solidification of a polymer precursor against a solid surface while the other by solidification on the liquid-gas interface. It is known to those skilled in the art that the surface quality of the two optical surfaces formed under such different circumstances may differ profoundly in both optical and biological respects.

Wichterle in U.S. Pat. No. 4,846,832 describes another manufacturing method of the intraocular lens where the posterior side of the lens has the shape of the solidified liquid meniscus (presumably approximating a flat ellipsoid shape with negative polyfocality) while the anterior side is formed as an imprint of the solid mold shaped as a second order surface that may implicitly include also a hyperbolic surface. Again, we can note that each of the optical surfaces is created differently—one by solidification of a polymer precursor against a solid surface while the other by solidification on the liquid-gas interface.

Stoy '283 discloses modifying the method described by Wichterle '732 using a two part mold, one part being similar to the Wichterle's mold while the other being used to form a modified meniscoid of a smaller diameter on the anterior lens surface. The meniscoid optical surface is of the same character as the meniscoid resulting from Wichterle '732, albeit of a smaller diameter and, therefore, probably closer to a spherical surface than an ellipsoid surface. In any case, such a surface has negative polyfocality. The posterior side is formed as an imprint of the solid mold shaped as a second order surface that may include a hyperbolic surface while the other optical surface is formed by solidification of the liquid polymer precursor on the liquid-gas interface.

Michalek and Vacik in PCT/CZ2005/000093 describe an IOL manufacturing method using a spin-casting method in open molds. Molds filled with monomer mixture spin along their vertical axis while polymerization proceeds. One of the optical surfaces is created as the imprint of a solid mold surface while the other is formed by the mold rotation. The imprinted surface has the shape formed by rotation of the conic section along the vertical axis (which may include hyperboloid shape). The other surface is shaped as a meniscoid modified by the centrifugal force that will transfer some of the liquid precursor from the center toward the periphery. In the case of the convex meniscus, the centrifugal force will flatten the center and create a steeper curvature in the periphery, i.e. increase the spherical aberration of the surface. In the case of a convex meniscus, the centrifugal force will create a meniscus with smaller central radius and modify the surface to approximate something between spheric and parabolic shape. In any case, the hyperbolic aberration cannot be achieved for either a convex or concave meniscoid surface.

Sulc et al. in U.S. Pat. Nos. 4,994,083 and 4,955,903 discloses an intraocular lens with its anterior face protruding forward in order to be in permanent contact with the iris that will center the lens. Both posterior and anterior surfaces may have the shape obtained by rotation of a conical section around the optical axis (sphere, parabola, hyperbole, ellipse). The iris-contacting part of the lens is a hydrogel with very high water content (at least 70% and advantageously over 90% of water) that is inherently soft and deformable. Therefore, the optical surface deformed by the contact with iris cannot be exactly a conic section surface, but a surface with a variable shape that will depend on the pupil diameter, probably close to a sphere with a somewhat smaller central radius. Namely, this situation is similar to the lens from another reference that achieves decrease in the central diameter by pressing a deformable gel-filled lens against a pupil-like aperture in an iris-like artificial element (Nun in U.S. Pat. No. 7,220,279). Nun '279 does not mention or imply use of hyperboloid optical surfaces. Cummings in U.S. Pat. Publ. Nos. 2007/0129800 and 2008/0269887 discloses a hydraulic accommodating IOL in which a liquid is forced into the internal IOL chamber by action of cilliary apparatus causing thus change of the optical surface and accommodation.

Hong et al. in U.S. Pat. No. 7,350,916 and U.S. Pat. Publ. No. 2006/0244904 disclose a aspheric intraocular lens with at least one optical surface having a negative spherical aberration in order to compensate the positive spherical aberration of the cornea. The negative spherical aberration is achieved by hyperbolic shape of the optical surface.

Hong et al. in U.S. Pat. Publ. No. 2006/0227286 discloses optimal IOL shape factors for human eyes and defines the optimum lens by a certain range of "shape factors" from −0.5 to +4 (the shape factor being defined by Hong as the ratio of sum of anterior and posterior curvatures to their difference), and at least one of the optical surfaces is advantageously aspherical with conic constant between −76 and −27.

Hong et al. in U.S. Pat. No. 7,350,916 describes an IOL with at least one of the optical surfaces having a negative spherical aberration in a range of about −0.202 microns to about −0.190 microns across the power range.

SUMMARY OF THE INVENTION

In at least one aspect, the present invention provides an artificial lens implantable into the posterior chamber of human eye for replacement of the natural crystalline lens, the lens (referring to the FIG. 3) having a main optical axis 1A; the central optical part 2 and the peripheral supporting part 3; the overall shape of the implant being defined by its anterior surface 4, posterior surface 5 and the transition surface 6 between the upper boundaries of the anterior and posterior surfaces 7A and 7B of the implant; having the central anterior optical surface 8A with boundary 9A and anterior apex 10A; the central posterior optical surface 8B with boundary 9B and posterior apex 10B; and anterior peripheral supporting surface 11A and posterior peripheral supporting surface 11B.

Artificial lens implantable into the posterior chamber of human eye for replacement of the natural crystalline lens that simulates as closely as practicable the shape, size, optical properties and material properties of an NCL while respecting the need for surgical implantation through a small incision.

The artificial lens according to at least one embodiment of the invention has at least the posterior surface approximating the shape and size of the posterior surface of the natural lens in order to achieve substantially complete contact with the posterior capsule of the eye. At least the part of the artificial lens according to our invention that is contacting the posterior capsule is made from a transparent flexible hydrogel material approximating the optical, hydrophilic and electrochemical character of tissue forming the natural lens. The anterior side is designed to avoid a permanent contact with iris.

In at least one embodiment, the anterior surface is shaped to avoid a permanent contact with the iris with the anterior peripheral supporting surface 11A being concave.

In at least one embodiment, the artificial lens according to the invention has at least the major parts of its anterior and posterior surfaces, including both optical surfaces, defined by rotation of one or more conic sections along the optical axis and formed by solidification of a liquid polymer precursor in contact with a solid wall of a mold, preferably a hydrophobic plastic mold.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 5A-5C illustrate top views of exemplary lenses with the optical surfaces divided into two or more optical zones.

FIGS. 6A to 6C are cross-sectional views of alterative lens in accordance with the invention composed from two or more materials.

DETAILED DESCRIPTION OF THE INVENTION

Figure 1:
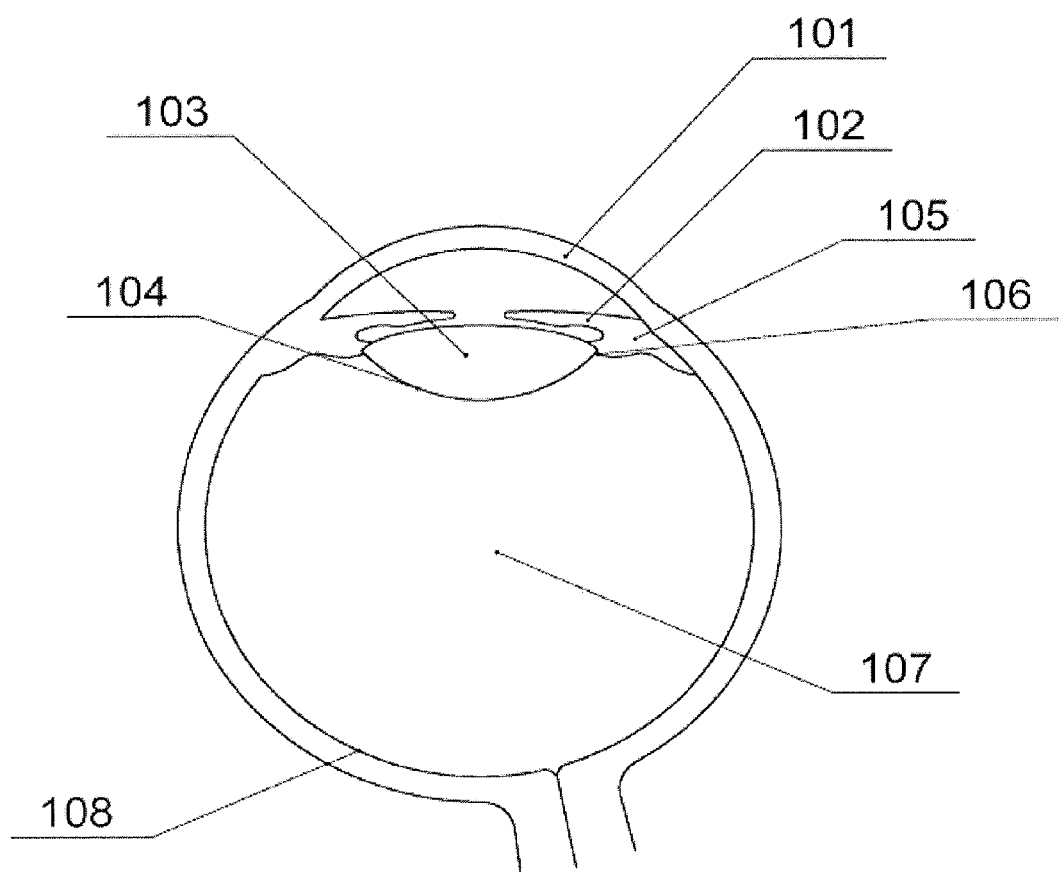
FIG. 1 illustrates the internal arrangement of the eye with main structures including the cornea, sclera, iris, NCL, vitreous body, retina and the suspensory apparatus of the lens (capsule, zonules and cilliary muscle)

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

The NCL has a very complicated structure that develops over time. One of the structural features is asphericity of posterior and anterior surfaces of the NCL 103. As established in recent years E. L. MARKWELL et al, MRI study of the change in crystalline lens shape with accommodation and aging in humans, Journal of Vision (20110 11(3);19, 1-16; M. Dubbelman et al, Change in shape of the aging human crystalline lens with accommodation, Vision Research 45 (2005), 117-132; F Maims et al, Radius of curvature and asphericity of the anterior and posterior surface of human cadaver crystalline lens, Experimental Eye Research 78 (2004), 39-51; M. Dubbelman et al, The shape of the aging human lens: curvature, equivalent refractive index and the lens paradox, Vision Research 41 (2001) 1867-1877, both anterior and posterior surfaces of a young human lens are hyperbolic and can be characterized by the equation:

$$Y-Yo=X^2/\{Ro*(1+(1-h*(X/Ro)^2)^0.5)\} \quad 1$$

where Y is the coordinate in the direction of the main optical axis 1A, X is the distance from the main optical axis 1A, Yo is the apex position on the main optical axis 1A, Ro is the central radius of curvature and h is the conic constant (or the shape parameter). The Eq. 1 describes any conic section curve depending on the shape parameter h value: it is a parabola for h=0, a circle for h=1, hyperbole for h<0, prolate ellipse for 0<h<1 and oblate ellipse for h>1.

It has been found that for a typical young human NCL, the anterior surface is more hyperbolic than the posterior surface, that hyperbolicity increases significantly with accommodation, and that the human lens grows with age and its hyperbolicity decreases so that an old NCL may become substantially spherical.

The referenced studies mapped dimensions of typical NCL for selected population samples. According to these references, a typical human lens anterior central radius ranges from about 5 to 13 mm and the average anterior conic parameter is about −4 (ranging from about −22 to +6). The posterior central radius ranges from about 4 to 8 mm and the average posterior conic parameter is about −3 (ranging from about −14 to +3).

The central thickness of a young, relaxed NCL ranges typically from about 3.2 mm to about 4.2 mm, increasing with age and/or with the near-focus adjustment to a thickness from about 3.5 mm to about 5.4 mm. The posterior part depth of the NCL is typically the same as, or larger than the anterior part depth. Therefore, the sagittal depth of the posterior lens surface is typically from about 1.75 mm to about 2.75 mm on equatorial diameter from about 8.4 mm to about 10 mm. This defines the basic dimensions of the posterior capsule in its "natural" state.

Although the above references do not state any particular connection between the geometry and optical properties of the NCL, we have found by mathematical modeling that the hyperbolic surfaces turn a lens polyfocal, with the refractive power maximum at its center and gradually decreasing toward the periphery. One direct consequence we expect from such a polyfocality is a large focal depth of the lens so that a near object can be projected on the retina even without any particular lens shape change. Another implication of the modeling is that the average refractive power of the lens increases with decreasing aperture. Therefore, we conclude that the near focus can be improved by pupil constriction (this so called "pupillary reflex" or "near myosis" that can be actually clinically observed at near focus). Another consequence of the natural lens hyperbolicity is the capability of the human (and particularly young) brain to naturally neuroadapt to, and correctly interpret images formed by projection through a hyperbolic lens onto retina.

This accommodative mechanism utilizing certain type of the polyfocality perhaps deserves some more explanation:

Lenses with at least one hyperbolic surface demonstrate a "hyperbolic aberration" that is opposite of the spherical aberration: rays incoming through the center are bent into a focal point that is closest to the lens, and the focal point becomes progressively further from the lens for rays incoming in increasing distance from the lens center toward the lens periphery.

Therefore, the lens with hyperbolic surface is positively polyfocal: it has the shortest focal distance (i.e., highest refractive power) at its center, and the focal distance increases (i.e., refractive power decreases) from the center toward the lens periphery. The focal range of a hyperbolic lens can be rather large and is controllable by so called conic constant or shape parameter defining the hyperbolic surface shape.

Figure 2:
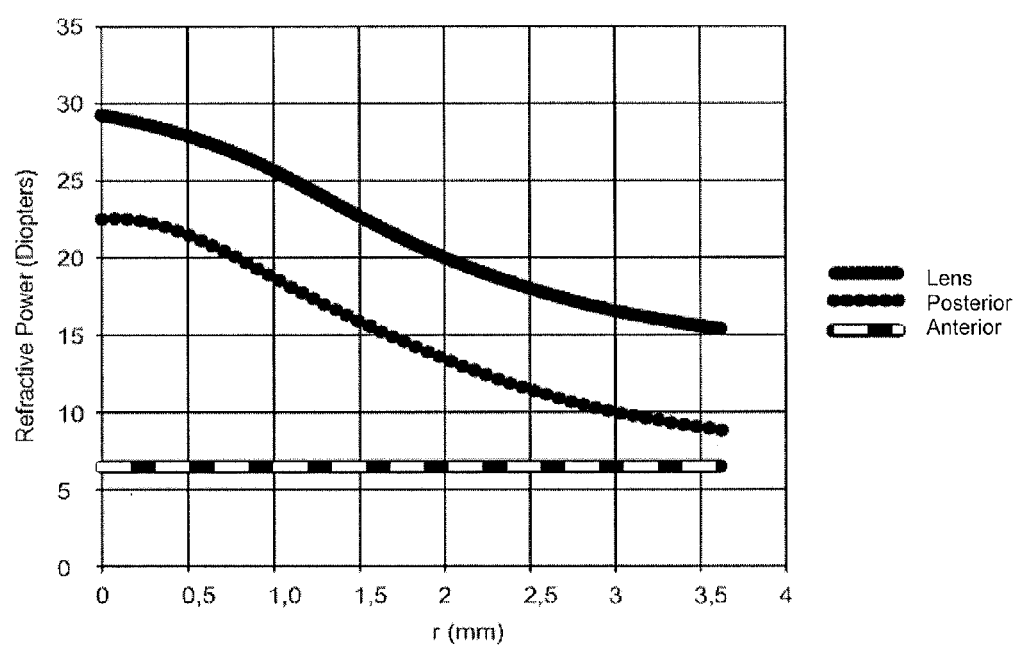
FIG. 2 illustrates distribution of refractive power in a lens with one hyperbolic surface.

Examples of the distribution of refractive power in a lens with hyperbolic surface is shown in FIG. 2 where local refractive power in Diopters $m^{-1}$ are plotted against the distance from the optical axis in mm.

We assume, based on our studies, that the positive polyfocality and its changes in the natural lens assist the eye to accommodate in several ways:

It projects on the retina simultaneously images of all objects in the field of view in all distances covered by the focal range of the lens. This substantially increases the depth of the focus of the eye since all objects create a well-focused image (accompanied by many dis-focused images that our brain learns to suppress).

The natural lens increases its hyperbolicity due to the accommodation, which further increases the focal range of the lens and, therefore, the depth of the focus still further.

The eye helps to focus on near objects by narrowing the pupil. This so called "pupillary reflex" or "near myosis" has two consequences: first, it decreases the aperture and thus increases depth of the focus of the eye as the optical system (narrowing aperture blocks rays that are far from the axis and coming in at sharp angles with respect to the axis); and it increases the average refractive power of the lens by using only its central portion with the highest refractive power.

It is obvious from our studies that near myosis can assist the near focus only for lenses with hyperbolic aberration, i.e. with positive polyfocality. It has little effect in monofocal parabolic lenses, and it is counterproductive in lenses with negative polyfocality: spherical or elliptical (e.g., meniscoid) lens becomes weaker lens with lower refractive power by the near myosis rather than a stronger lens that is needed for near focus.

An artificial lens according to our invention is a hydrogel device implantable into the posterior chamber of human eye for replacement of the natural crystalline lens. It is designed to mimic or replicate essential physiological and optical functions of natural lens without creating problems that earlier attempts could cause in some situations. It is important to recognize that this is achieved by a novel thoughtful combination of features that might have been individually, or in different combinations, applied previously with a lesser success. The natural lens also achieves its function due to its balanced combination of features rather than to a single feature.

The features contributing to the overall function and combined according to our inventions include size and shape of the implant; material properties; surface properties; optical properties; implantation method; and manufacturing method. We will describe the various features below and provide exemplary configurations of how individual features mutually interact to provide beneficial effect. It is important to recognize that the implant may combine several of the described features to achieve desirable effects, however, the invention is not limited to the exemplary configurations described below and includes various combinations of features.

Figure 3A:
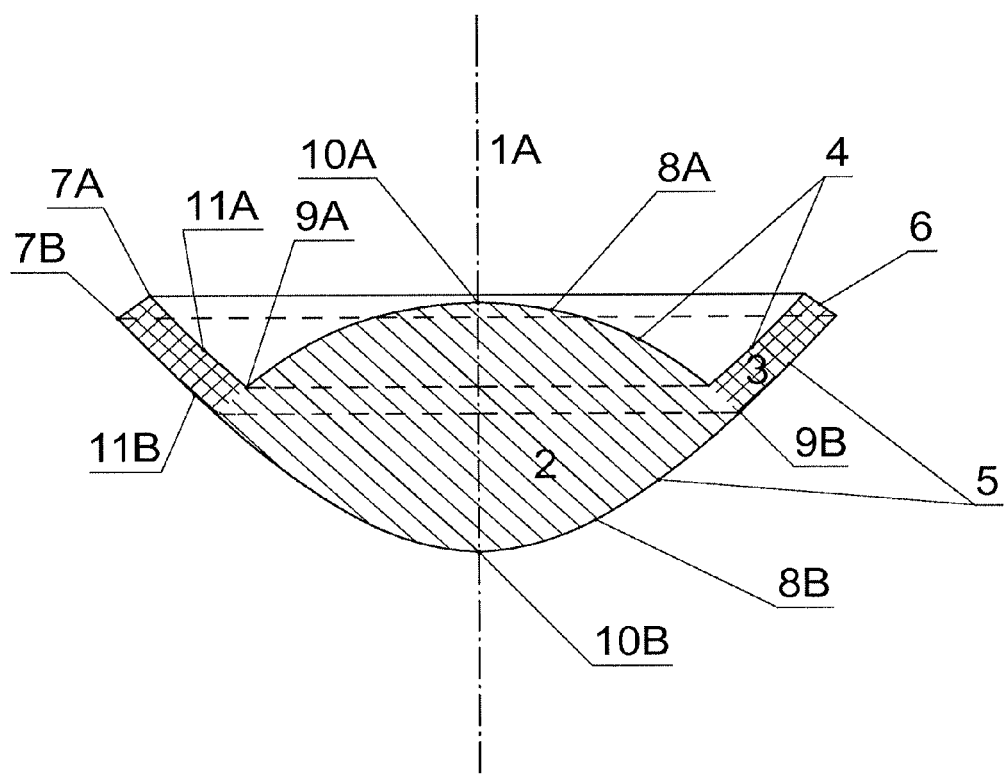
FIG. 3A is a cross-sectional view of a bioanalogic intraocular lens according to an exemplary embodiment of the invention.
Figure 3B:
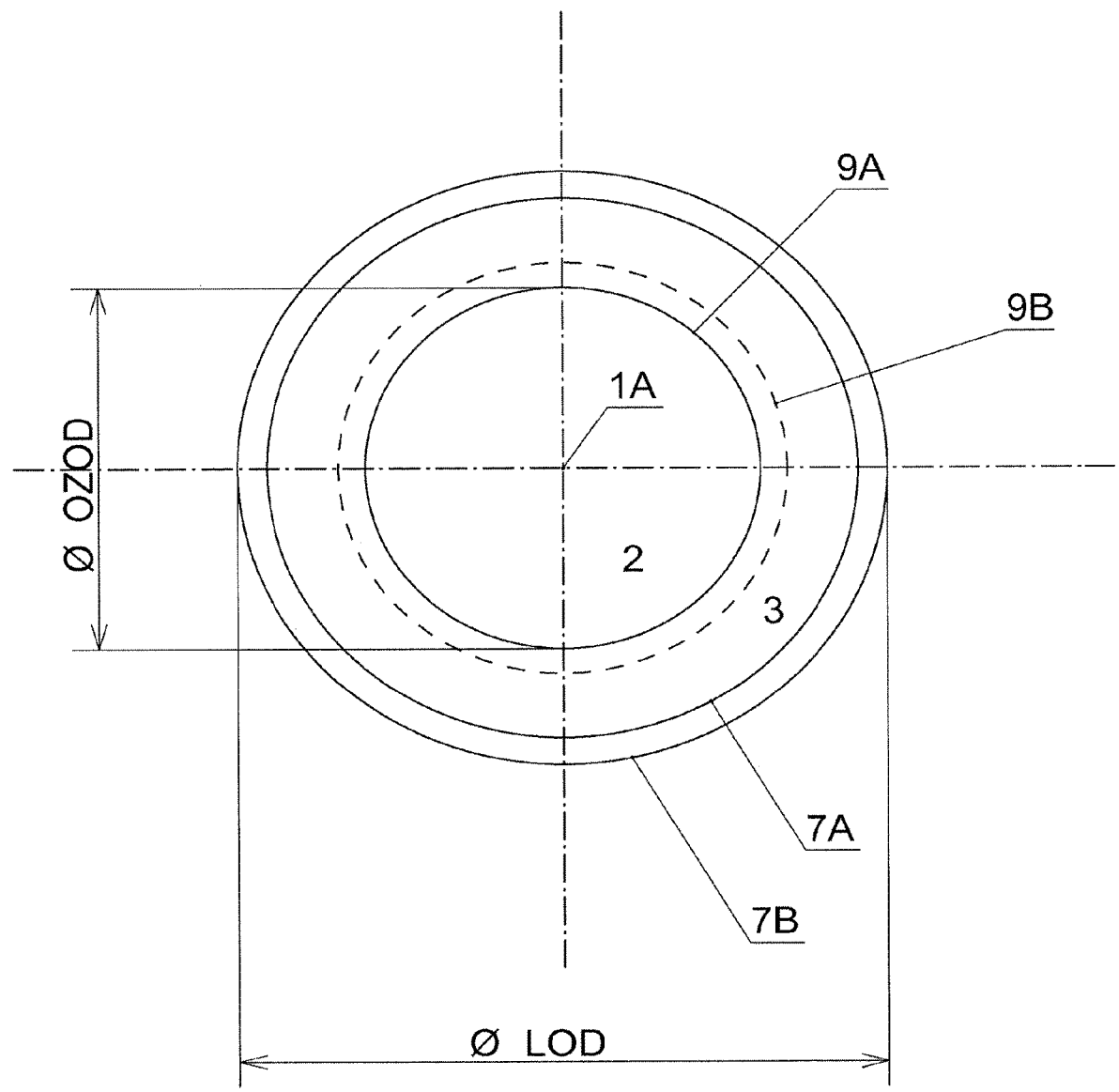
FIG. 3B is a top view of the lens of FIG. 3A.

Referring to FIGS. 3A and 3B, the implant has a main optical axis 1A with a central optical part 2 and a peripheral supporting part 3. The overall shape of the implant is defined by its anterior surface 4, posterior surface 5 and the transition surface 6 between the upper boundaries 7A and 7B of the anterior and posterior faces, respectively. Each face is composed of two or more surfaces. The anterior central optical surface 8A has boundary 9A and central posterior optical surface 8B has boundary 9B. Each of the surfaces may be divided into two or more zones with the boundary between them (denoted 13A and 13B in FIGS. 5A to 5C) being circles, straight lines or otherwise defined shapes. The apexes of the central anterior optical surface 10A and central posterior optical surface 10B are positioned on the main optical axis 1A. The anterior peripheral supporting surface is 11A and the posterior peripheral supporting surface is 11B.

The boundaries 7A and 7B are distinguishable as a discontinuity on the top of the anterior and posterior surfaces 4 and 5, respectively. Such a discontinuity lay in the inflexion point of the surface in the direction of the optical axis, or a in a point of discontinuity of the second derivative of the surface in the direction of the optical axis. The boundary can be rounded and continuous, but advantageously it is formed by a sharp rim or edge. The advantage of the sharp edge is in forming the obstacle to migration of cells such as fibroblasts along the capsule surface (the usual reason for posterior capsule opacification).

The overall lens diameter is defined as the larger diameter of the boundaries 7A and 7B. The lens optical zone diameter is defined as the smallest diameter of the boundaries 9A and 9B. The posterior sagittal depth is the vertical distance between the posterior apex 10B and the plane defining the posterior boundary 7B. Central thickness is the distance between apexes 10A and 10B. Anterior depth is the vertical distance between the anterior apex 10A and the plane defining the anterior boundary 7A.

Figure 4A:
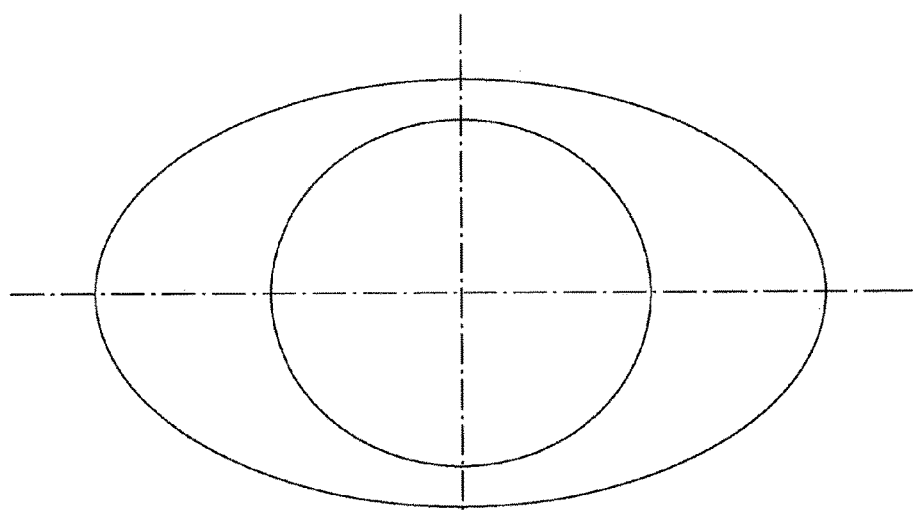
FIG. 4A is a top view of another exemplary embodiment of a lens with a circular optical part and elliptical support part.
Figure 4B:
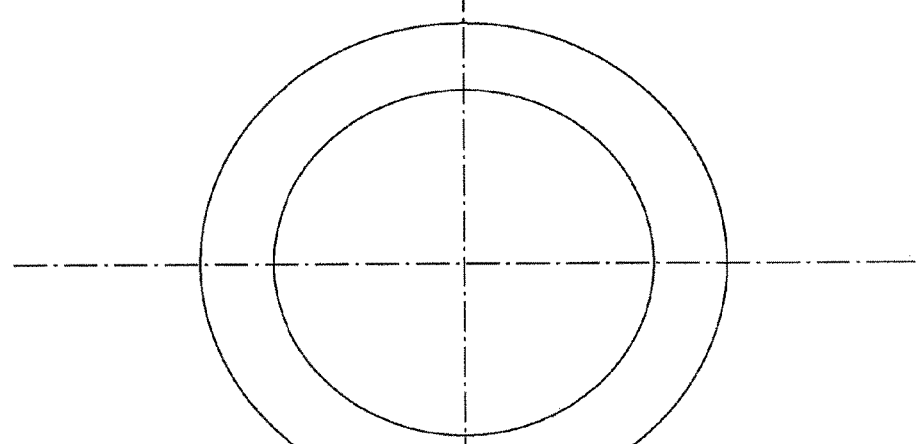
FIG. 4B is a top view of another exemplary embodiment of a lens with a circular support part truncated by a single straight cut.
Figure 4C:
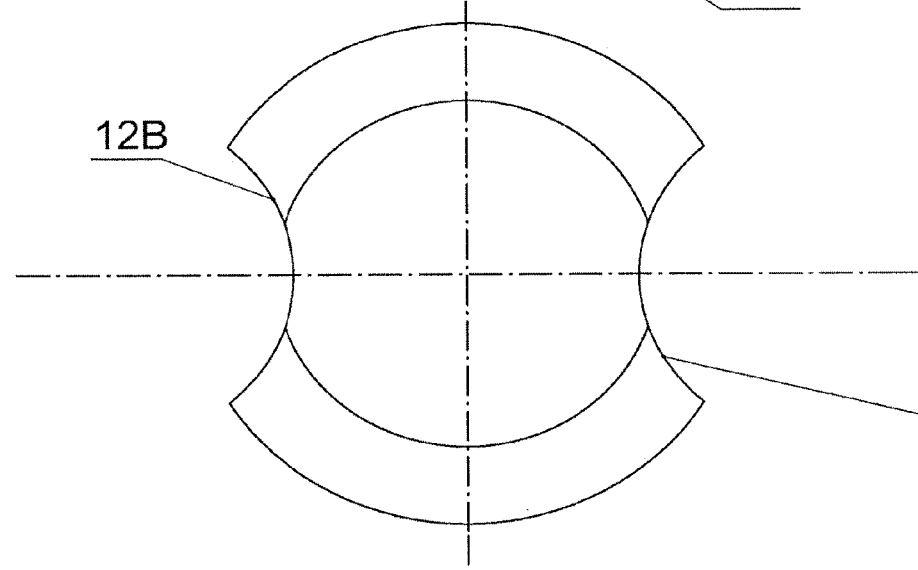
FIG. 4C is a top view of another exemplary embodiment of a lens with a circular support part truncated by two symmetric crescent cuts.
Figure 4D:
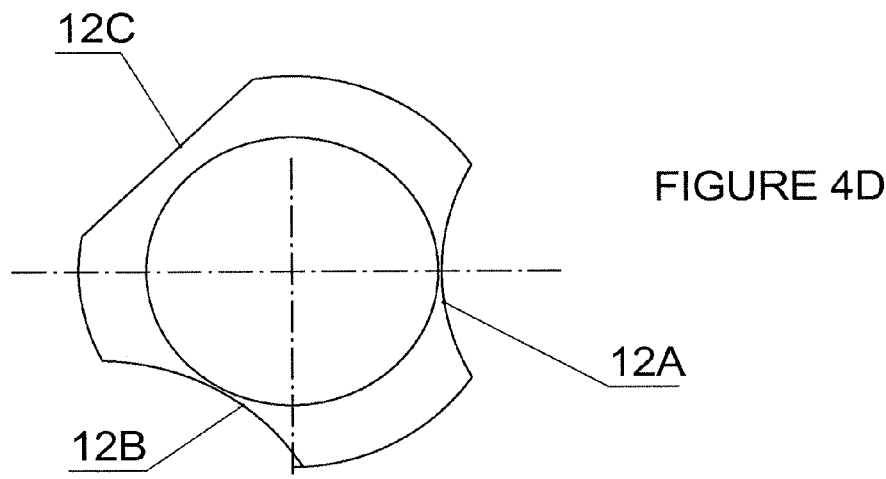
FIG. 4D is a top view of another exemplary embodiment of a lens with a circular support part truncated by one straight and two crescent cuts.
Figure 4E:
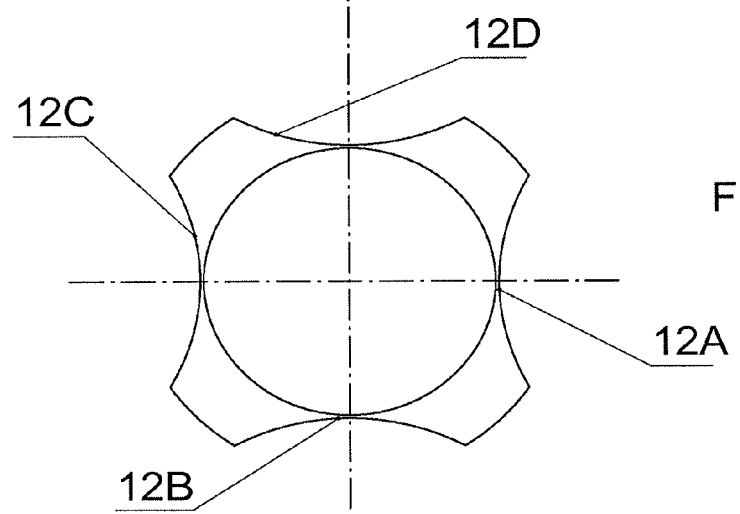
FIG. 4E is a top view of another exemplary embodiment of a lens with a circular support part truncated by four symmetric crescent cuts.

The main optical axis 1A may be the axis of symmetry in the case that boundaries 7A and 7B, as well as boundaries 9A and 9B, are defined by circles in the plane perpendicular to the optical axis, and if the central optical part 2 is symmetrical and e.g., does not have any cylindrical component. Such implant with symmetric circular footprint is shown in FIG. 3B. However, the rims and boundaries may have other than circular footprint, e.g. elliptical as shown in FIG. 4A, or may have the footprint shaped as a truncated circle in FIGS. 4B to 4E with single, double, triple or quadruple truncating cuts 12A to 12D. These truncated footprint shapes serve several purposes:

They provide better access into the space behind the lens during the implantation. It is important to clean this space well in order to remove any viscoelastic polymers or lubricants or other auxiliary agents before the surgical incision is closed.

They prevent rotation of the lens after the capsule shrinks around the IOL. This is particularly important for toric lenses.

They facilitate folding and insertion through a small incision.

Figure 4F:
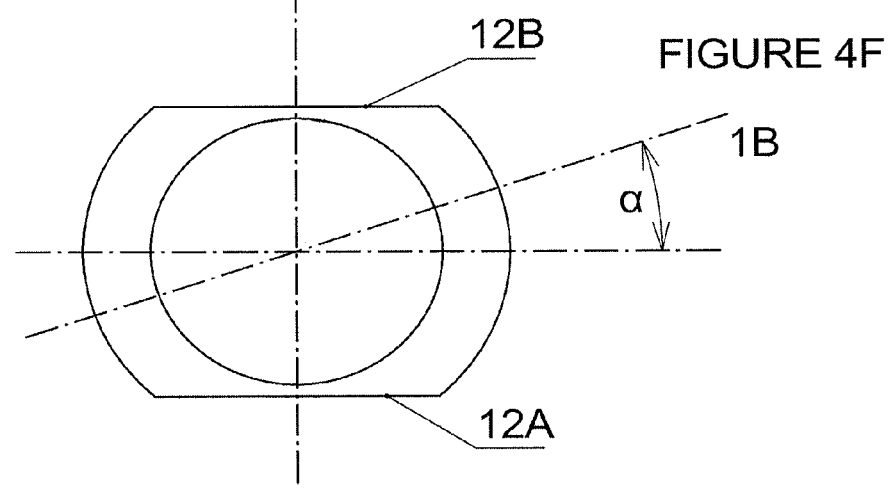
FIG. 4F is a top view of another exemplary embodiment of a lens with a circular support part truncated by two straight parallel cuts and the cylindrical lens with cylinder axis 1B in the angle α with regard to the cuts direction.

In the case that the optics has a cylindrical component, then the cylinder axis 1B will be positioned in a defined way with respect to the asymmetry of the outside rim, e.g. be in the angle $\alpha$ to the truncating cuts 12A and 12B as shown in the FIG. 4F. Needless to say that the truncating cuts 12A to 12D may not be necessarily straight cuts, but may be suitably formed to e.g. a crescent shape, and their number may be even higher than 4. Also, the truncating cuts may not be of the same length or positioned symmetrically. It can be appreciated that the footprint with truncated rim will facilitate folding of the implant and its insertion through a small surgical incision. In addition, the asymmetric rim footprint will prevent the implant rotation once the capsule settles around it. This is particularly important for toric lenses with a cylindrical component designed to compensate for astigmatism.

The posterior surface 5 is shaped and sized to approximate the shape and size of the posterior surface of the natural lens and to achieve contact with at least the major part of the posterior capsule of the eye. This is important for several reasons:

The implant will keep the posterior capsule in its natural shape, unwrinkled and smooth for the optimum optical performance;

The tight contact between the capsule and the implant will prevent migration of fibroblasts that could cause the posterior capsule opacification; this is particularly effective if the posterior surface is highly hydrated and carrying fixed negative charge.

The implant will occupy the space vacated by the posterior side of the natural lens and keep thus vitreous body from advancing forward and prevent thus the decrease of the pressure of vitreous body against retina (which could facilitate retinal detachment and/or cystoic macular edema).

It should be noted that the intimate contact between the implant and posterior capsule is beneficial particularly if the contacting surface of the implant is hydrophilic and carrying fixed negative charge in order to prevent capsular fibrosis and its consequent stiffening, opacification and contraction that would interfere with the implant function (or could even dislocate it), as will be described hereinafter.

In the preferred embodiment of the invention, at least the major part of the posterior surface 5 is formed by a generally smooth convex surface formed by rotation of conic sections around the optical axis, or a combination of such surfaces. The peripheral part is preferably formed by a conic surface or a hyperboloid surface, while the central optical surface is preferably hyperboloid, paraboloid or spherical surface (or a combination thereof). The sagittal depth of the posterior surface (i.e. the vertical distance between the posterior central optical surface apex 10B and the boundary of the posterior surface 7B, measured on the main optical axis 1A) should be larger than 1.1 mm in order for lens to perform its function well. To perform well in the whole refractive range, the posterior sagittal depth should be larger than 1.25 mm, advantageously larger than 1.75 mm and preferably larger than 2 mm, but in any case less than about 2.75 mm.

The overall outer diameter of the implant (LOD) is important for its centricity, position stability and capsule-filling capability. The outer diameter of the posterior surface 5, i.e. the largest dimension of the posterior outer boundary 7B (in the plane perpendicular to the main axis 1A) should be larger than 8.4 mm, desirably at least 8.9 mm and preferably at least 9.2 mm. The largest outer diameter permissible is about 11 mm, but desirably should be lower than 10.75 mm and preferably at smaller than 10.5 mm. The considerable flexibility in the outer dimensions is allowed by several factors—flexibility of the lens, and particularly flexibility of the outer peripheral supporting part 3 that can accommodate various capsule sizes and capsule contraction without deforming the central optical part 2.

Figure 5A:
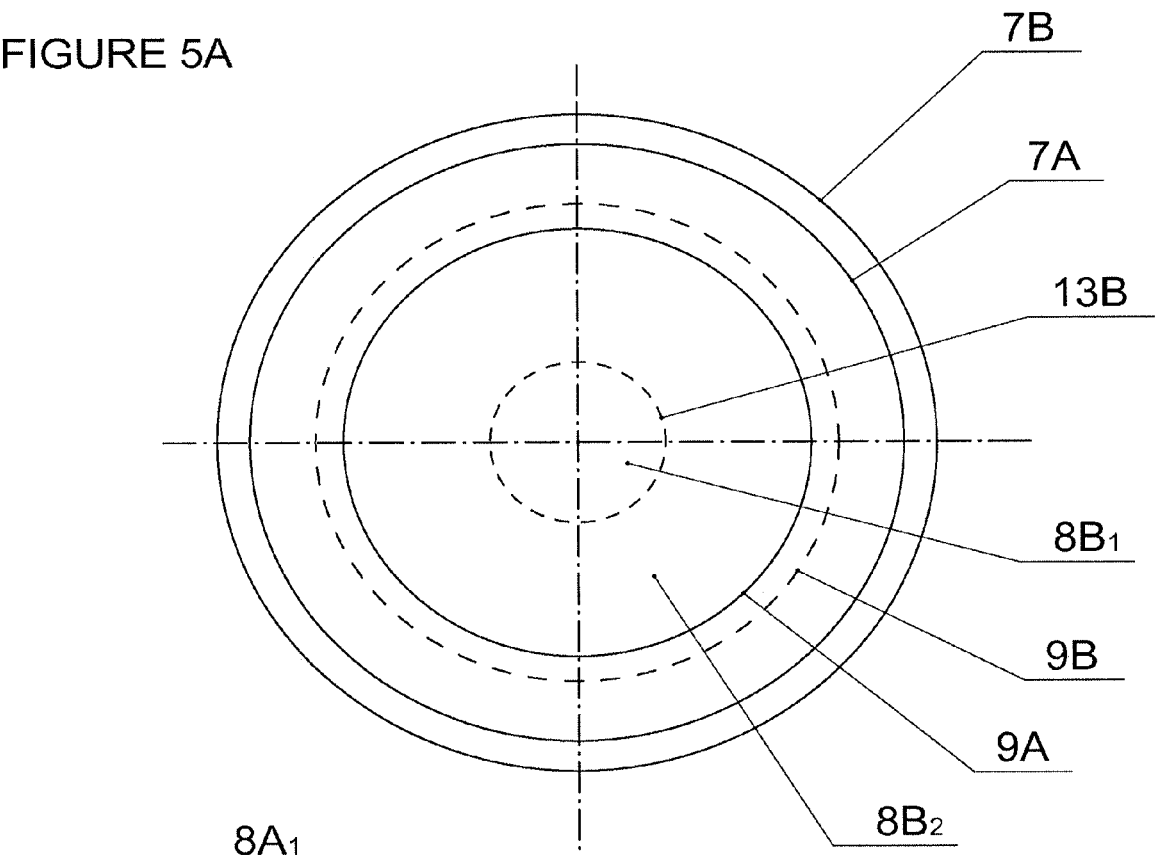
Figure 5B:
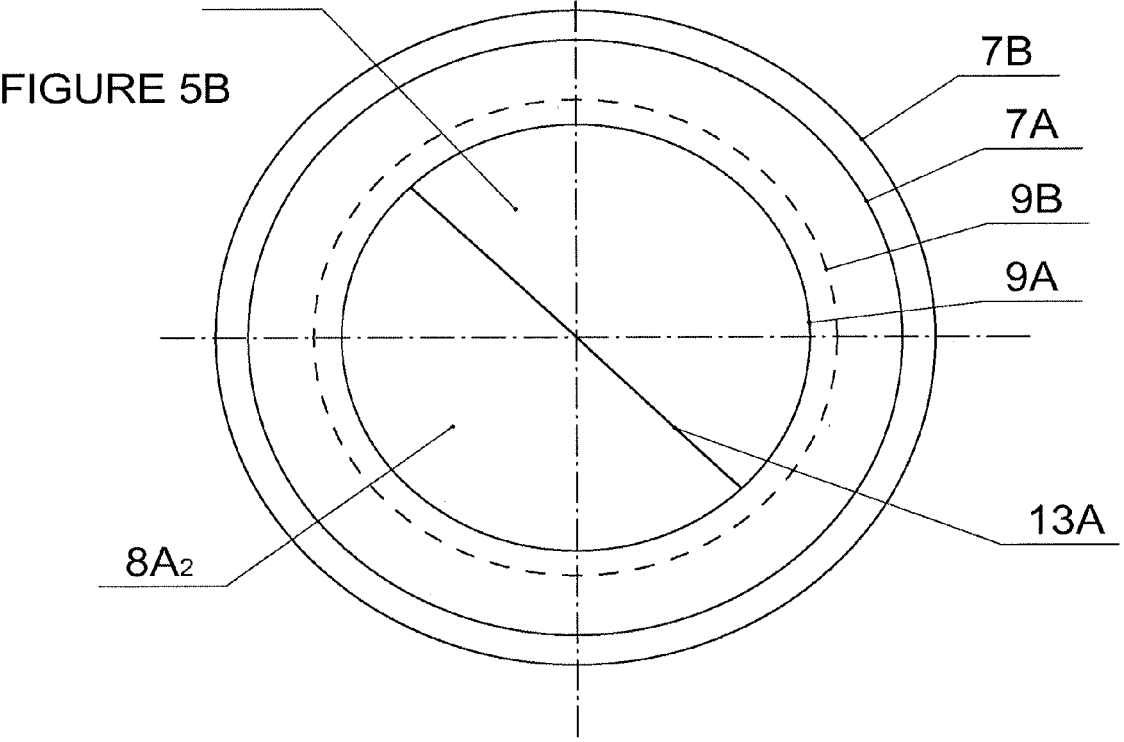

The central optical surfaces may consist of one or more zones with different geometry. The zones may be concentric, in which case the posterior boundary 13B between them in the FIG. 5A will be circular. Zones may also be divided by straight boundaries, in which case the zones may have crescent or wedge footprint. Various examples are shown in FIGS. 5A to 5C. The zones may be on the anterior or posterior optical surface. FIG. 5A shows the posterior optical surface is divided by the boundary 13B into two concentric optical zones—the central optical zone 8B1 and the outer optical zone 8B2. For instance, the posterior optical surface of the central optical zone 8B1 may be a spherical or parabolic zone used for the sharp near vision, while the hyperbolic outer zone serves for intermediate and far distance vision. Alternatively, both zones may have hyperboloid surfaces with different central radii Ro and/or different conic constants. Each optical surface may be also divided into more than two zones. The example in FIG. 5B shows the top view of the lens which anterior optical surface 8A is divided by a straight boundary 13A into two optical zones of equal area 8A1 and 8A2. Each of those zones has different shape with different optical parameters. The example in FIG. 5C shows a top view of a lens with anterior optical surface 8A divided by two straight boundaries 13A and 13B into four paired optical zones 8A1 and 8A2, each having a different area and different optical parameters. For instance, 8A1 may have higher refractive power that 8A2 and serve for near focus. One of the zones may have a cylindrical component.

Both optical surfaces (or their zones or segments) are surfaces formed by rotation of a conical section along the optical axis, or by a combination thereof. One or both optical surfaces may contain one or more spherical optical zones. Advantageously, at least one of the optical surfaces comprises at least one hyperbolic surface, preferably in the outer optical zone. Preferably, both optical surfaces comprise at least one hyperbolic zone each. Such hyperbolic surface resembles the surfaces of the NCL and mimics some of its beneficial optical properties. Even more preferably, both posterior and anterior optical surfaces are hyperbolic surfaces or a combination of two or more concentric hyperbolic zones. Lenses with at least one hyperbolic surface have so called hyperbolic aberration, the very opposite of spherical aberration of lenses with spherical, ellipsoid or meniscoid surfaces. The lenses with hyperbolic aberration have highest refraction in the center and gradually decreasing with distance from the optical axis. (In lenses with spherical aberration the refractive power increases with distance from the optical axis.) The hyperbolic aberration helps the eye to accommodate through several mechanisms described above.

In order to mimic the optical properties of the NCL, conical constants of the anterior and posterior optical surfaces are selected so that the refractive power of the central optical part 2 generally decreases from the highest value at the optical axis to the lowest value at the periphery of the central optical part 2.

The steepness of the refractive power decrease with the distance from optical axis is dependent on the shape parameter (conic constant) of the hyperbolic surface. The conic parameter should be selected that the average decrease of the refractive power is between −0.25 Dpt/mm and −3 Dpt/mm, advantageously between −0.5 Dpt/mm and −2.5 Dpt/mm and preferably between about −1 Dpt/mm and −2 Dpt/mm.

The posterior central radius of curvature (at the point where the optical axis intersects the posterior apex) is advantageously from 2.5 to 8 mm, and preferably from about 3.0 to 5 mm. The conic constant of the posterior surface is advantageously selected from the range of about +3 to about −14 reported for NCL, preferably from about −1 to −8.

The central radius Ro of the anterior optical surface 8A is selected to be either larger than about +3 mm or smaller than about −3 mm, and preferably larger than from about +5 mm or smaller than about −5 mm.

The conical constant of the anterior optical surface 8A is selected from the range from +6 to −22 reported from human NCL, preferably from the range between about −1 to −8 mm.

The anterior optical surface 8A may be formed partly or fully by a spherical surface or a parabolic surface. In that case the central posterior optical surface 8B should be preferably hyperbolic with the conic parameter selected in such a range so that the whole lens has hyperbolic aberration.

Preferably though, at least the major part of the anterior optical surface 8A is a hyperboloid surface, particularly the outer optical zone. The central optical zone of the anterior optical surface having diameter between about 1.5 to 4 mm, advantageously between about 2 and 3.5 mm, can be formed by parabolic or spherical surface in order to further improve the near focus resolution.

FIG. 2 shows schematically one example of the preferred optical profile of the lens according to our invention. It should be appreciated that different eyes require different refractive power of the implanted lens.

Most of the current IOLs are not bioanalogic since they are designed to simulate just the basic optical function of NCL, i.e. to provide the basic refractive power needed to focus a distant object on retina. Depending on the specific eye, the basic refractive power is usually between 15 and 30 Dpt, with some deviations on either side. This requirement can be met by a substantially monofocal (usually spherical) rigid lens located somewhere near of the principal plane of the NCL. Since most detailed images are projected onto a relatively small part of retina (macula) located on the optical axis, and since many of our activities are performed at small eye aperture (constricted pupil), most IOLs are significantly smaller than the NCL (4.5 to 6 mm for most IOLs as opposed to 9.5 to 10.5 mm for the NCL). The small size of optics is preferred by some IOL manufacturers for easier adaptation of such IOL for implantation through a small incision. For the same reason, most IOLs are made from a soft, elastic material that allows implantation through a small incision in a deformed (folded, rolled, etc.) shape. This deformability has no relation to the optical function, however.

Small size of optics has its disadvantages, however. IOL edges may reflect light at large pupil opening (e.g., during night driving) and cause glare, halos and other adverse effects. Besides, a small optic cannot project all peripheral and off-axis rays that NCL does, particularly at a large pupil opening. Lastly, a small size optics interferes with clear visibility of retinal periphery that is sometimes needed for diagnostics and treatment. For those reasons, the large optics similar in size to NCL is preferable over a smaller one that is used in most of the current IOLs Importantly, the whole large optical zone has to have well defined geometry to be optically useful. Lenses with meniscoid optical surfaces have poorly defined shape particularly in the peripheral region. This may cause unexpected and disturbing optical phenomena.

Some modern IOLs are designed to simulate to some extent the accommodation or pseudoaccomodation of the NCL (i.e. allowing the eye to focus on both far and near objects). Various IOLs use different means to achieve this goal: some are using bifocal, multifocal or polyfocal optics; others are using designs allowing anterior-posterior shift of the IOL optics with respect to the eye; or allow change of optical power by changing mutual position between two lenses. Some lenses even change the refractive power due to liquid transfer within the lens driven by pressure of cilliary muscles and/or vitreous body, change of head position or by a miniature pump.

These designs are sometimes rather intricate contraptions, very different in size, shape and material properties from the NCL. This makes them susceptible to various problems, such as fibrosis of the capsule or cell ingrowth or protein deposits on their surfaces that interfere with their function. In addition, their increased bulk and complicated design interferes with the need of all modern IOLs to be implantable through a small incision. This requires designs with small-diameter optics and use of materials with high refractive index that are more reflective than the NCL, increasing thus the glare and halo problems.

In most cases, these lenses are using optics of a small diameter, typically 4.5 to 6 mm, with slender, flexible "haptics" to position the optics in the center of the optical path. In addition, deformable materials are used to allow folding or rolling for implantation through a small incision. The surface properties of such IOLs are sometimes modified to achieve better biocompatibility (e.g., A. M Domschke in the U.S. Pat. Publ. No. 2012/0147323, J. Salamone et al in the U.S. Pat. Publ. No. 2008/0003259).

This common design allows folding the IOL for the implantation through a relatively small incision (usually 2 to 3 mm) However, the small IOL size has its own drawbacks:

The small optics with diameter 6 mm or less may not fully replace the crystalline lens of diameter 9 to 10.5 mm if eye aperture is large due to poor light conditions (causing night glare, halos, limited peripheral vision etc.) or if the IOL becomes decentered (causing the "sunset syndrome" or other problems);

Small optics cannot project all peripheral and off-axis rays the NCL does, reducing thus the imaging performance particularly at large pupil openings (needed for e.g., night peripheral vision);

Small optics may complicate or even prevent retinal examination and treatment (which may be important particularly in the case of diabetics).

In addition, a small IOL size leaves essentially vacant the space that was originally occupied by the much larger NCL. Consequently, the vitreous body is allowed to advance and its pressure against the retina is partly relieved. This may cause an increased probability of retinal detachment after the cataract surgery as reported by J. A. Rowe, J. C. Erie, K. H. Baratz et al. (1999). "Retinal detachment in Olmsted County, Minn., 1976 through 1995". Ophthalmology 106 (1): 154-159. The same effect may also cause or facilitate Cystoid Macular Edema (CME). See Steven R. Virata, The Retina Center, Lafayette, Ind.: Cystoid Macular Edema, WEB page.

There is another disadvantage of a small optics and the conventional IOL design with haptics: The IOL with optics suspended in the relatively vacant space by means of relatively fragile haptics may be sensitive to damage and/or dislocation in case of an accidental impact (fall on a slippery surface, car collision, a punch, etc.).

Some problems derived from a small bulk of IOLs and small-diameter optics are being addressed by IOL designs that fill the space vacated by NCL to a smaller or larger extent. There are several approaches to this, each with its own advantages and disadvantages:

Capsule-filling by a liquid that can solidify into a clear, flexible solid such as a silicone rubber. As long as the filler material has similar deformability as the NCL, it was expected that this approach would restore the natural lens accommodation (e.g., Gasser et al. in U.S. Pat. No. 5,224, 957). However, the materials used so far often cause fibrosis and opacification of the capsule. Besides, it is difficult to control the shape and optical parameters of the in situ formed IOL Implantation of a large, bulky IOL in a highly deformed shape that allow implantation through a reasonably small incision and substantially fills the capsule. This approach was tried with hydrophobic memory polymers that can be "frozen" in a highly deformed shape for implantation, and returns into the original functional shape upon heating to body temperature (Gupta in U.S. Pat. No. 4,834,750 and U.S. Pat. No. RE 36,150). However, the hydrophobic memory polymer is very foreign material and causes similar problems like the materials used to fill the capsule.

Similar approach was also tried with hydrogels. Very large IOLs, substantially mimicking size and shape of the natural lens, have been implanted into the vacated capsule (e.g., Wichterle '732 and Stoy '283). The problem of these particular IOLs was their peculiar optics. These lenses had meniscoid anterior optical surfaces that deviated strongly from the geometry of an NCL. The meniscoid shape was formed by solidification of a free surface of the monomer mixture, and there was a problem with control of the optical properties of such IOLs. In addition, these lenses were often too bulky for implantation through a small incision. Moreover, some of the hydrogels used in these lenses lacked the fixed negative charge, and such hydrogels have tendency to calcify sometime after their implantation. Some other capsule-filling lenses (Sulc et al. '083 and '903) had anterior protrusions touching the iris and stabilizing thus the lens in the approximately central position but causing various problems such as blockage of the liquid flow, deformation of lens optics and iris erosion.

Another approach was implantation of a hollow lens (or a lens shell) that was filled after implantation by a liquid solidifying in situ (e.g., Nakada, et al. in U.S. Pat. Nos. 5,091,121 and 5,035,710).

Another approach was implantation of dual-optics IOLs with two lenses, one being in contact with anterior and the other with the posterior capsule, both lenses being kept apart by flexible members or connectors (U.S. Pat. Nos. 4,946,469; 4,963,148; 5,275,623; 6,423,094; 6,488,708; 6,761,737; 6,764,511; 6,767,363; 6,786,934; 6,818,158; 6,846,326; 6,858,040; 6,884,261).

Such implants filling essentially the whole capsule of the original crystalline lens have also some problems:

Unless made from extremely biocompatible materials with similar hydration and negative charge as NCL, the anterior face of the IOL may touch the iris and cause its erosion, depigmentation, bleeding or inflammation.

Some materials are made more biocompatible by having high equilibrium water content. However, that decreases their refractive index far below the optimum value (the value for young NCL).

Important for the IOL is not only the shape and optics type, but also its material. An NCL is composed of an intricate a natural hydrogel structure comprising water, salts, and polymeric component containing collagenous proteins, polysaccharides and proteoglycans. Importantly, the polymeric components contain a considerable concentration of acidic ionizable groups, such as carboxylates or sulfates. These groups provide the lens material with a fixed negative charge. The hydration and the negative charge influence the interaction between the NCL and proteins in the intraocular fluids. Furthermore, its surface properties affect the interaction between the lens and cells. It is known that synthetic hydrogels containing surface with a fixed negative charge do not attract the proteins and cells and make hydrogel more resistant to calcification (Karel Smetana Jr. et al, "Intraocular biocompatibility of Hydroxyethylmethacrylate and Methacrylic Acid Copolymer/Partially Hydrolyzed Poly(2-Hydroxyethyl Methacrylate)," Journal of Biomedical Materials Research (1987) vol. 21 pp. 1247-1253), and are not recognized as a foreign body by immune system (Karel Smetana Jr. et al, "The Influence of Hydrogel Functional Groups on Cell Behavior", Journal of Biomedical Materials Research (1990) vol. 24 pp. 463-470). Although many IOL manufacturers avoid materials with carboxylate groups based on the assumption that carboxylates attract calcium ions and thereby cause calcifications, there are several references to hydrogel IOLs containing carboxylate groups (Wichterle '732, Sulc et al. '083 and '903, Stoy in in U.S. Pat. No. 5,939,208, Michalek and Vacik in '093).

Carboxylate groups may be uniformly dispersed in the hydrogel, or concentrated mainly on the surface forming a gradient of swelling and charge density, as described e.g. in Stoy '208 and Sulc et al. U.S. Pat. No. 5,158,832. Typically, the NCL material contains, on average, about 66% by weight of water. However, the NCL is structured with denser core and more hydrated jacket and the NCL hydration changes with age and from individual to individual. Therefore, one cannot assign a single water content value to the NCL other than average.

Similarly, various layers of the NCL have different refractive indices. The refractive index of the lens varies from approximately 1.406 in the central layers down to 1.386 in less dense layers of the lens. See e.g. Hecht, Eugene. Optics, 2nd ed. (1987), Addison Wesley, ISBN 0-201-11609-X. p. 178. Therefore, the optically meaningful equivalent refractive index, or ERI, is given as the characteristic of the NCL. Both refractive index and water content change with the lens age. Average ERI=$1.441-3.9\times10^{-4}\times$AGE, decreasing thus from about 1.441 at birth to about 1.414 at 70 years. See M. Dubbelman et al. "The Shape Of The Aging Human Lens: Curvature, Equivalent Refractive Index And The Lens Paradox", Vision Research 41 (2001) 1867-1877, FIG. 9.

In addition, the ERI increases with accommodation by about 0.0013-0.0015 per Diopter. See M. Dubbelman et al, "Change In Shape Of The Aging Human Crystalline Lens With Accommodation", Vision Research 45 (2005), 117-132 Ref pp. 127-128. One can speculate that this change of refractive index is related to a change (decrease) of water content due to the lens deformation during the accommodation. Disregarding these complications, we will use the average ERI=1.42 unless stated differently.

Interesting to see that it is very difficult, if not impossible to find a synthetic hydrogel with same water content and—at the same time—refractive index as the NCL material. Specifically, a synthetic hydrogel containing 66% by wt of water would typically have a refractive index of about 1.395 rather than 1.42 that would be expected with hydrogel containing closer to 50% of water.

The average liquid contents for ERI=1.441 (very young average NCL) would be 40% of water while for ERI=1.414 (old average NCL) would need a hydrogel with water content about 55% by weight. Since we believe that for bioanalogic IOL material it is more important to simulate refractive index than water content of NCL, we have selected the desirable average water content range of the IOL according to an exemplary embodiment of the invention, to be between 40% and 55% by weight. Of course, this is the average water content—similarly as with the NCL, the lens may have various layers with different water contents, e.g. inner parts with higher refractive index and outer layers with lower refractive index.

A number of prior art references mention IOLs from hydrogels with high water content, however, they do not recognize the relation between the water content and the refractive index value. For instance, Wichterle '732 specifies the desirable refractive index value around 1.4 (broadly from 1.37 to 1.45, which is clearly impossible for known synthetic hydrogels with the specified water content: at least 60% and preferably 65 to 70% translates into the refractive index range from 1.39 to 1.405). The examples show formulations with a low content of carboxylate groups.

Sulc et al. '083 and '903 disclose water content at least 70% and advantageously at least 90% on the surface or its part, and mentions 55-70% water content in prior art IOLs. A core with higher and a casing with lower refractive index are mentioned, and the core may have the form of a Fresnel lens. The gradient of both hydration and refractive index is optionally obtained by NaOH treatment that achieves reorganization of the hydrogel covalent network. Example 1 of this reference shows an IOL with water content 88.5%, Example 2 shows the IOL with water content 81%, and Example 4 shows the lens with water content 91%. No water content is given for Example 3.

Charles Freeman in U.S. Pat. Publ. No. 2009/0023835 describes a hydrogel material with water content lower than 55% and refractive index higher than 1.41 and the sodium ion flux in the range of about 16 to about 20 micro.eq-mm/hr/cm$^2$, useful particularly for phakic posterior chamber IOLs. No carboxyl or acidic groups are mentioned, although their presence is known to increase the ion diffusion flux through the hydrogel.

Hydrogel character of the NCL material has some possible, less obvious but potentially important consequences: its water content is dependent on the pressure against the lens. Consequently, the NCL adjusted to the far distance may have a different water content, and therefore a different refractive index, than the relaxed lens adjusted to the near objects. Since the stress in the NCL adjusted for far distance is not distributed evenly, a gradient of swelling and gradient of refractive index may result. This will create subtle changes in the optical properties, in addition to the polyfocality of the NCL surfaces. These subtle changes may be important for our vision, and it will be difficult to replicate them otherwise rather than by using a hydrogel of similar physical-chemical and optical properties, as well as geometry similar to that of an NCL. In particular, the hydrogel of the NCL substitute should have a similar refractive index and capability to change water content by an external stress that can be reasonably expected to act on an NCL. Therefore, the hydrogel used in a bioanalogic IOL should have a hydraulic flow capability for water.

Therefore, at least the part of the implant contacting the posterior capsule is made from a transparent flexible hydrogel material approximating the optical, hydrophilic and electrochemical character of tissue forming the natural lens.

The anterior part of the IOL may interfere with, or even block the flow of the vitreous humor causing thus increase of IOP and ultimately glaucoma. This design often requires a preemptive iridectomy.

Unless made from extremely biocompatible materials with similar hydration and negative charge as an NCL, the large-area contact between the capsule and artificial materials used in current IOLs sometimes cause the capsule opacifications, fibrosis, etc. These problems are now being solved by the bioanalogic intraocular lens according to this invention.

The central optical part 2 is made of a deformable, elastic material, such as a hydrogel with equilibrium water content between about 35 and 65%, advantageously between about 38% and 55% and preferably between about 40% and 50% (all % are weight percent and equilibrium water content is water content in equilibrium with intraocular fluid, unless stated otherwise).

Deformability of the optical part is important both for the implantation through a small incision and for its accommodation function. The optical part may be constructed as a hydrogel shell with a core composed from a liquid or a soft gel, as shown in the FIG. 6A. FIG. 6A shows a cross-sectional view of a lens with the posterior hydrogel jacket 14, the softer core 15 and the anterior shell 16. The posterior hydrogel jacket 14 is advantageously integral with the peripheral supporting part 3 of the lens and contains the fixed negative charge at least on its posterior surface. The core 15 can be advantageously made from a hydrophobic liquid, such as mineral oil or silicone oil, or from a soft silicone or acrylic slightly cross linked gel that can be easily designed and created by those skilled in the art. Alternatively, the core can be made or a hydrophilic fluid or a soft hydrogel. The anterior shell 16 can be made from the same or different material as the posterior hydrogel jacket 14.

In one embodiment, the hydrogel jacket and the soft core 15 have essentially the same refractive index so that the major part of the refraction takes place on the outer optical surfaces of the lens rather than on its internal interfaces. This can be achieved e.g. by making the core from a silicone liquid or a silicone gel having refractive index around 1.42, and making the jacket from a hydrogel with water content between about 41 and 45% of water. By formulating the hydrogel correctly one skilled in the art can adjust the water content in the hydrogel to achieve the substantial match of the refractive indices. Alternatively, the core and the jacket can have different refractive indices so that part of the refraction takes place on the internal interfaces between materials.

Figure 6B:
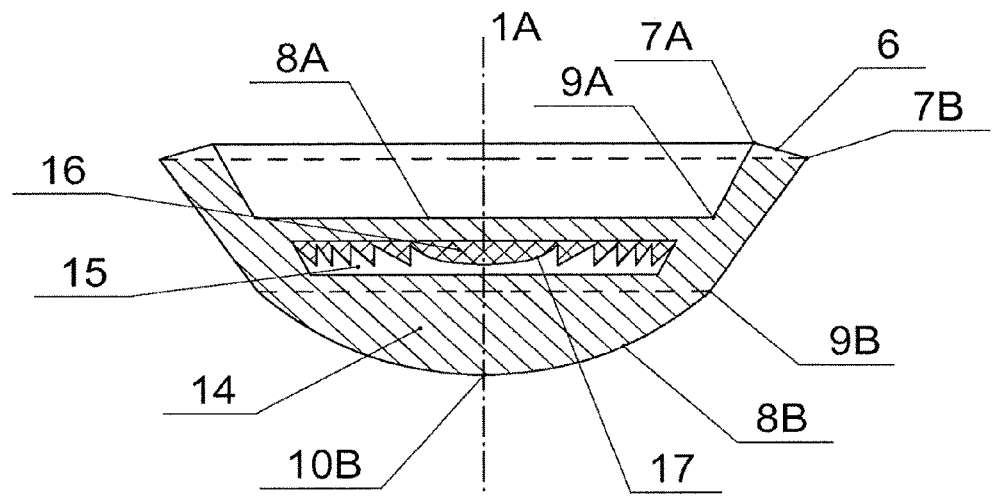

FIG. 6B a cross-sectional view of a lens with an internal interface between the core 15 and adjacent optical medium 16 that is shaped to form a compound lens, e.g. a Fresnel lens. The materials of core 15 and the optical medium 16 have different refractive indices, and one of them is advantageously a fluid that can improve both deformability and refraction. Advantage of this arrangement is the possibility to use hydrogels with high water content and low refractive index as the basic construction material, and yet achieve relatively low central thickness of the lens that allows implantation through a small incision.

Figure 6C:
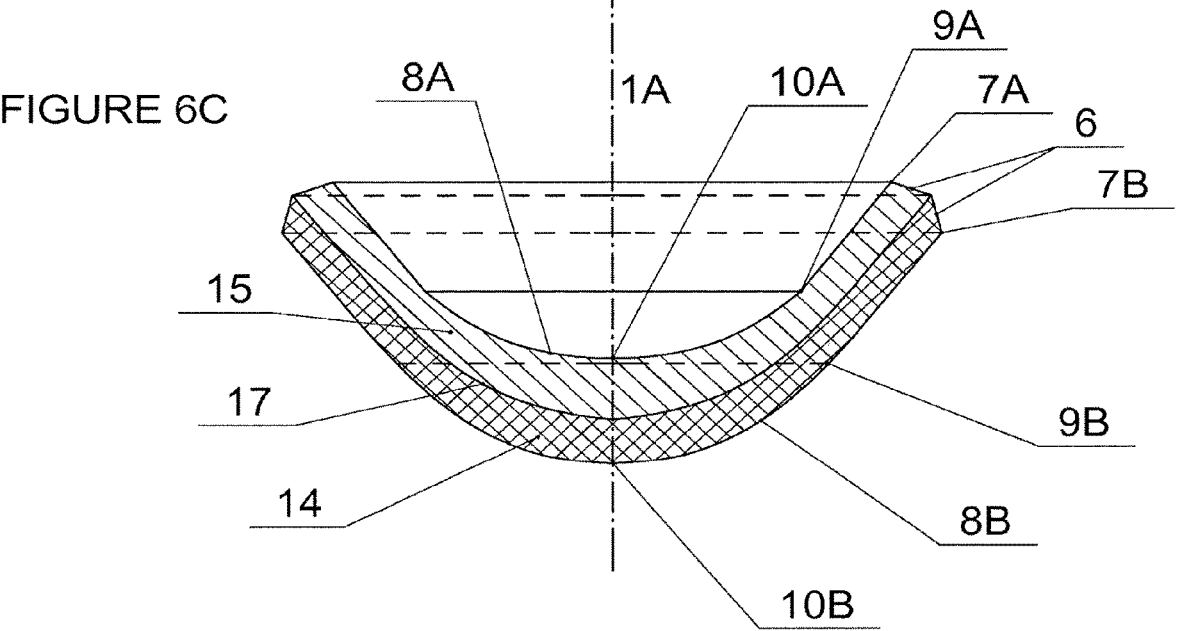

FIG. 6C shows an alternative design of the lens comprising two different materials. Material on the posterior side 14 is a hydrogel with high hydration rate and containing negatively charged groups. It is the same for the optical and supporting part. The anterior side material of core 15 is a material with lower water content and higher refractive index. The interface between the two materials is refractive.

Both central optical anterior surface 8A and central posterior optical surface 8B have a diameter larger than about 5.6 mm, advantageously larger than about 6.5 mm and preferably larger than about 7.2 mm. Optimum diameter of the larger of the two optical surfaces is larger than about 7.5 mm, advantageously about 8 mm to approximate the size of the NCL optics. Such a large optic is usually suitable for convex-concave or plano-convex central optical part 2. For a biconvex optical part, the anterior optical diameter is usually selected smaller in order to minimize the central thickness of the optical part. In any case, the diameter of the anterior optical surface 8A is advantageously not larger than the diameter of the central posterior optical surface 8B.

The central optical surfaces 8A and 8B are surrounded by boundaries 9A and 9B that are not necessarily circular. The boundaries 9A and/or 9B may be also elliptical or have a shape of a truncated circle, in order to facilitate the lens folding and implantation through a small incision. Non-circular optical surfaces are particularly suitable for lenses with a cylindrical component.

The posterior peripheral supporting surface 11B is formed by a convex surface, advantageously a hyperbolic or conical surface with the axis identical with the main optical axis 1A. This surface is highly hydrophilic and carrying a fixed negative charge due to a content of acidic groups such as carboxylate, sulfo, sulphate or phosphate groups. This combination of hydration and negative charge prevents a permanent adhesion to the capsule, prevents migration of cells, particularly fibroblasts, along the interface between the lens and the capsule, decreases irreversible protein adsorption, and discourages capsular fibrosis and opacification. The posterior peripheral surface is advantageously limited by a sharp edge 7B that further discourages cell migration toward the optical zone.

The anterior peripheral supporting surface 11A is a concave surface with its apex located on the optical axis and it is preferably symmetrical along the axis 1A. Advantageously it is a conical or hyperbolic surface with its axis coinciding with the main optical axis 1A. The surface is advantageously highly hydrophilic and carrying fixed negative charge in order to discourage cell adhesion and migration and anterior capsular fibrosis. The anterior peripheral surface is advantageously limited by a sharp edge 7A that further discourages cell migration.

The anterior and posterior peripheral supporting surfaces 11A and 11B together with the connecting surface 6 define the shape of the peripheral supporting part 3. The peripheral supporting part is convex on the posterior side and concave on the anterior side, the average distance between the two surfaces ranging from about 0.05 to 1 mm, advantageously from about 0.1 to 0.6 mm and preferably from about 0.15 to 0.35 mm. The optimum distance depends on the stiffness of the material that is dependent on water content, negative charge density, crosslinking density and other parameters.

Figure 7A:
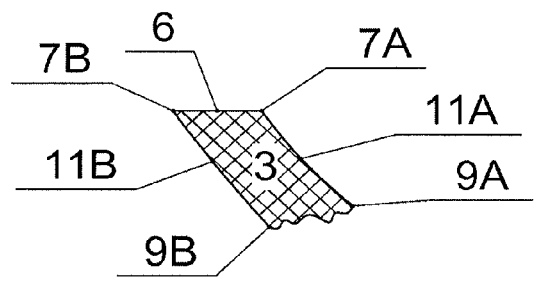
FIGS. 7A to 7C are expanded views illustrating alternative profiles of the supporting peripheral part of the exemplary lenses.

If the posterior and anterior surfaces are formed by surfaces of similar geometry, such as hyperbolic surfaces, then the peripheral supporting part 3 will have even thickness. The arrangement shown in FIG. 7A has the advantage to be readily deformable and adjustable to various sizes of the capsule, and two sharp edges 7A and 7B preventing migration of fibroblasts toward the optical zone.

Figure 7B:
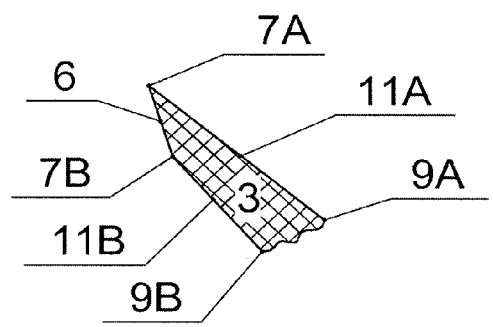
Figure 7C:
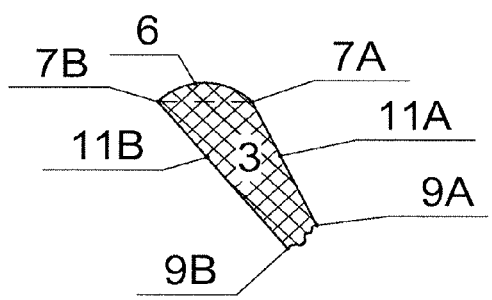

The peripheral supporting part 3 can be also made less or more deformable by increasing or decreasing its thickness from the rim toward the center, as shown in FIGS. 7B and 7C, respectively. These figures also show various alternative arrangements of edges 7A and 7B.

The anterior surface 4 of the implant is shaped to avoid any permanent contact with iris that could cause iris erosion, pupilar block, iris pigment transfer to the implant and other problems. Such a contact could also interfere with the flow of the intraocular fluid causing thus adverse changes of the intraocular pressure. It could also interfere with the contraction of the pupil as to prevent so called near myosis that helps the near focus both by the natural lens and by the implant according to our invention. Therefore, the anterior central optical surface 8A part is partially sunk due to the anterior peripheral supporting surface 11A concavity and due to positioning the boundary 9A under the plane defined by the anterior boundary 7A. The central anterior surface 8A is a plane, a convex surface or a concave surface with its anterior apex 10A not exceeding the uppermost point of the lens (the higher of 7A and 7B) by more than about 0.25 mm, advantageously not exceeding the upper rim at all and preferably having the anterior apex 10A bellow the uppermost point 7A by at least 0.1 mm.

At least the major part (including the central optical surfaces 8A and 8B) of both anterior and posterior surfaces 4 and 5 are defined by rotation of one or more conic sections around the main optical axis 1A. wherein the term "conic section" includes a segment of a line for purpose of this application. The surfaces defined by the rotation will include a plane perpendicular to the axis and conical surface symmetrical by the main optical axis 1A. The peripheral supporting part is convex on the posterior side and concave on the anterior side, the average distance between the two surfaces ranging from about 0.05 to 1 mm, advantageously from about 0.1 to 0.6 mm and preferably from about 0.15 to 0.35 mm.

In at least one embodiment, the lens according to the invention is manufactured by solidification of liquid polymer precursors. In the preferred embodiment, the solidification takes place in contact with a solid mold, particularly a mold made of a hydrophobic plastic. It can be appreciated that the surface microstructure of a polymer depends on the environment in which its solidification took place. The surface microstructure will be different if the solidification occurs on the solid liquid interface that if it takes place on the liquid-liquid or liquid-gas interface. Preferably, at least all optical surfaces are created by solidification of the precursor on a solid interface. Even more preferably, whole surface of the implant is formed by solidification of a liquid precursor against a solid surface, particularly a hydrophobic plastic surface. Preferred plastic for the mold is a polyolefin, and particularly preferred plastic is polypropylene. The polyolefin has low polarity and has low interaction with highly polar monomers that are used as hydrogel precursors. Likewise, the hydrogel formed by the liquid precursor solidification has very low adhesion to the mold surface and can be cleanly detached without even a microscopic surface damage. This is important for both optical properties and for long-term biocompatibility of the implant.

Manufacturing a relatively large lens of a precise shape by molding is difficult. It is recognized by those skilled in the art that any solidification of the liquid precursor is accompanied by the volume shrinkage that may even exceed 20 percent. In a closed mold of a constant volume, such a shrinkage will prevent copying of the internal mold surface and cause formation of vacuoles, bubbles, surface deformities and other imperfections. This is the main reason why the meniscus casting methods described above were used for IOL molding. Other inventors have described a method and a mold design allowing the excess of monomers to be transported from adjacent spaces by the suction created by the volume contraction (Shepherd T., U.S. Pat. No. 4,815, 690). However, this method cannot be used in cases where the liquid precursor gellifies at a low conversion (e.g., 5 to 10 percent) due to the crosslinking polymerization.

Figure 8:
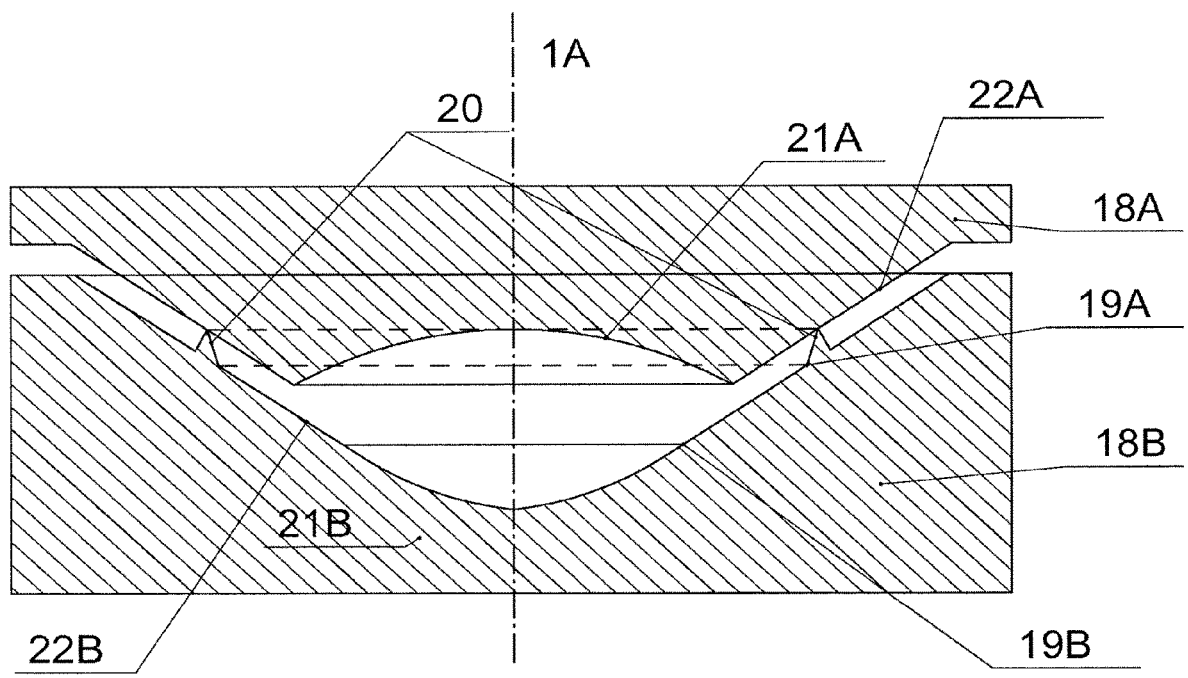
FIG. 8 illustrates the schematic arrangement of the mold for production of a lens in accordance with an exemplary embodiment of the invention.

We have discovered a different method for the volume shrinkage compensation, namely, decrease of the internal mold cavity volume due to the deformation of certain mold parts. The mold depicted in FIG. 8 is composed from two parts 18A and 18B, the part 18A being used for molding the anterior surface 4 and the part 18B for molding the posterior surface 5.

The shaping surface 19B of the part 18B has a shape needed to form the posterior optical surface 8B of the lens. The peripheral part 22B of the molding surface has a diameter larger than the diameter of the lens and advantageously a hyperboloid or conical shape The part 18A has the shaping surface 19A that is divided into the central part 21A shaping the anterior optical surface 8A of the lens, and the peripheral part 22A of the diameter larger than the diameter of the lens. The peripheral part 22A has advantageously a hyperboloid or conical shape. The peripheral surface 22A is substantially parallel to the corresponding surface 22B of the part 18B.

The diameter of the molding the mold parts 18A and 18B are substantially larger than diameter of the lens and advantageously they are the same. One of the surfaces for 22A or 22B is equipped with a relatively thin and deformable barrier 20 with inner surface corresponding to the geometry of the surface 6 of the lens. The height of the part 20 is typically between about 0.05 mm and 1.3 mm, and its thickness is lesser than its height. The profile of the part 20 is advantageously wedge-like or triangular. At least one of its surfaces is advantageously parallel to the optical axis 1A. The barrier 20 may be separate from the parts 18A and 18B, but advantageously it is an integral part of one of them. Advantageously, this part 20 is located on the concave surface 22B. In a preferred mode of the operation, the liquid precursor is filled into the concave mold part 18B in a slight excess to reach over the barrier 20, and then it is covered with the part 18A. The mold is constructed in such a way that the only contact between parts 18A and 18B is via the part 20. The solidification of the precursor generates its contraction and the consequent decrease of the pressure in the mold cavity. At a low conversion, the additional liquid precursor is pulled into the mold cavity. Once the gel-point is reached due to the crosslinking, the precursor cannot flow anymore. The decreased pressure will cause deformation of the part 20 and decrease of the distance between parts 18A and 18B and the consequent decrease of the molding cavity volume. The two-part mold for the IOL according to the invention is preferably made by injection molding from a polyolefine, advantageously from polypropylene.

The preferred liquid precursor for the invention is a mixture of acylic and/or methacrylic monomers with crosslinkers, initiators and other components known well to those skilled in the art. The preferred precursor composition comprises a mixture of acrylic and/or methacrylic monoesters and diesters of glycols where monoesters are hydrophilic components and diesters are crosslinkers. The preferred precursor also comprises acrylic and/or methacrylic acid or its salts. It advantageously comprises also a UV absorbing molecule with a polymerizable double bond, such as methacryloyloxybenzophenone (MOBP). Other possible derivatives or acrylic or methacrylic acid are their esters, amides, amidines and salts.

Also part of the hydrogel structure are ionizable groups bearing a negative charge, such as carboxylate, sulfate, phosphate or sulfonic pendant groups. They may be introduced by copolymerization with appropriate monomers bearing such groups, such as methacrylic or acrylic acid. In this case, the ionogenic functional will be uniformly dispersed in the hydrogel. Particularly advantageous are hydrogels with ionogenic groups concentrated mainly on the surface with the consequent gradient of swelling and charge density. Such gradients can be created by after-treatment of molded lenses, e.g. by methods are described in Stoy '208 and Sulc et al. U.S. Pat. Nos. 5,080,683 and 5,158,832. In embodiments, the synthetic hydrogel contains ionizable functional groups selected from the group consisting of carboxyl group, sulpho-group, sulphate group, and phosphate group in an average concentration from about 0.15 molar % to about 5 molar %.

Other methods include, e.g. grafting of monomers comprising ionogenic groups on the lens surface. It is understood that only a part of the lens surface may be treated to contain high concentration of ionogenic groups, or that different parts of the surface may be treated by different methods.

The lens according to the invention can be implanted in the deformed and partly dehydrated state. The controlled partial dehydration can be achieved by contacting lens with a suitably hypertonic aqueous solution of physiologically acceptable salts, such as chlorides, sulfates or phosphates magnesium or monovalent ions, such as sodium or potassium. Salt concentration can be adjusted to achieve hydration between about 15% and 25% by weight of the liquid. The lens in the hypertonic solution can be advantageously sterilized by autoclaving.

Another method for preparing the hydrogel lens for implantation through an incision with reduced size is plastification of the hydrogel by a non-toxic organic water-miscible solvent, such as glycerol or dimethylsulfoxide, in such a way that the plasticized hydrogel has softening temperature above ambient but lower than eye temperature. Such composition and process is described e.g. in Sulc et al, U.S. Pat. No. 4,834,753 that is hereby incorporated by this reference.

The lens according to at least one embodiment of the invention is advantageously implanted in the state of the osmotic non-equilibrium to adhere to the tissue temporarily. The osmotic non-equilibrium allows the lens centering by adhering it against the posterior capsule while the capsule shrinks around it. Once the lens is enveloped by the capsule, its position is stabilized. The osmotic non-equilibrium can be achieved in various ways: soaking the lens prior to the implantation in a hypertonic salt solution, e.g. in a solution of 10% to 22% by wt. NaCl, advantageously 15% to 19% by wt.; replacing water prior to the implantation by a smaller concentration of a water-miscible solvent, such as glycerol or dimethylsulfoxide; or implanting the lens in the state in which the iogenic groups are not fully ionized, i.e. in the acidic state prior to the neutralization, and letting the neutralization proceed spontaneously in situ by positive ions from the body fluids. The lens achieves its osmotic equilibrium spontaneously in hours to days after the implantation.

The lens shape is being formed preferably by crosslinking copolymerization of methacrylic and/or acrylic esters and salts in the closed two-part mold.

The shape of the lens can be adjusted after the molding by removing some part of the lens, e.g. by cutting of part of the supporting part, by drilling the lens outside the optical zone etc. The shape adjustment can be made in the hydrogel or the xerogel (i.e. non-hydrated) state. We have found that the negatively charged hydrogel material even allows use of methods developed primarily for living tissues (incl. NCR), such as ultrasonic phacoemulsification, cauterization or femtosecond laser treatment. These methods allow shape adjustment even in fully hydrated hydrogel state. The femtosecond laser may be used even formation of cavities inside the hydrogel lens that can be used to form a new refractive members in the lens, for instance as a refractive cylindrical lens for astigmatism compensation. In the case that the matter removed by the shape adjustment (e.g., by a laser treatment) is water-soluble and substantially non-toxic, such an optical adjustment can be conceivably achieve even post-operatively in situ. The composition of the hydrogel in at least the treated part of the lens should be advantageously based on esters of polymethacrylic acid. It is known that such polymers are capable of depolymerization to their parent monomers (such as 2-hydroxyethyl methacrylate or methacrylic acid) that are well soluble, easily diffusible compounds of low toxicity. Other polymers, such as polyacrylates, polyvinyl compounds or polyurethanes do not have this advantage.

The invention is further illustrated by the following Examples that are meant to provide the additional information without limiting the scope of our invention.

Example 1

The following monomer mixture was prepared: 98 weight parts of 2-hydroxyethyl methacrylate (HEMA), 0.5 w.p. of triethyleneglycol dimethacrylate (TEGDMA), 1 w.p. of methacryloyloxybenzophenone (MOBP), 1 w.p. of methacrylic acid, 0.25 w.p. of camphorcquinone (CQ) and 0.05 w.p. of trieathanolamine (TEA). The mixture was de-aired using by carbon dioxide and filled into two-part plastic molds shown schematically in FIG. 8 where 18B is the part of the mold for molding the a posterior lens surface, 18A is the part of the mold to shape the anterior part of the surface of the lens. Both parts are injection molded from polypropylene (PP). The shaping surface 19B of the part 18B has shape formed by two concentric hyperboloids. The central part of the surface has the diameter 3 mm, central radius of 3.25 mm and conic constant −3.76 while the peripheral is hyperboloid with central radius of 3.25 mm and conic constant −6.26. The molding surface is equipped with a protruding circular barrier 20 on diameter 8.5 mm that has asymmetric triangular profile, height 0.2 mm. This lip is designed to shape the connecting surface 6 in FIG. 3A.

The part 18A has the shaping surface 19A that is divided into the central part 21 of diameter 6.8 mm and the peripheral part 22A of the diameter 13 mm. The peripheral part is formed by a hyperboloid with the central radius 3.25 mm and the conic constant −6.26. The peripheral hyperbolic surface is parallel to the corresponding surface of the part 18B. The central portion of the part 18A has the central radius of curvature −20 mm and conic constant h=1.

About 0.1 ml of the monomer mixture is pipetted into the part 18B, then it is covered by the part 18A that is carefully centered and pressed gently against it by a small weight. The only direct contact between the parts is the circular contact between the barrier 20 and the peripheral part of 22A. The mold is then illuminated for 10 minutes by a blue light at the wavelength 471 nm. The light initiates polymerization of the monomers accompanied by gelling at a relatively low conversion and by volume contraction that is roughly proportionate to conversion. The contraction of the soft gel creates a mild vacuum that pulls both parts of the mold together. The conical peripheral part 22A of the mold 18A presses against the barrier 20, deforms it slightly and closes to the part 18B to reduce the volume of the molding cavity. This compensates for the volume shrinkage due to the polymerization. The described mold design is particularly suitable for production of relatively bulky IOLs from materials with high polymerization contraction that achieves gel-point at a relatively low conversion.

The mold parts are separated and the xerogel lens, the exact copy of the mold cavity, is neutralized by solution of sodium bicarbonate and extracted with isotonic solution. The linear expansion factor between the xerogel and hydrogel lens is 1.17. After evaluation of optical properties the lens was immersed in the 18% by weight aqueous solution of NaCl in a sealed blister package and sterilized by autoclaving.

Example 2

The following monomer mixture was prepared: 94 weight parts of 2-hydroxyethyl methacrylate (HEMA), 0.5 w.p. of triethyleneglycol dimethacrylate (TEGDMA), 4.5 w.p. of methacryloyloxybenzophenone (MOBP), 1 w.p. of methacrylic acid and 0.25 w.p. of dibenzoylperoxide. The mixture was de-aired using nitrogen carbon and filled into two-part plastic molds shown schematically in FIG. 8. The shaping surface 19B of the part 18B has a shape formed by two concentric surfaces. The central part of the surface has the diameter 3 mm, central radius of 3.00 mm and conic constant 1 while the peripheral section is a hyperboloid with central radius of 3.25 mm and conic constant −6.26. The molding surface is equipped with a protruding circular barrier 20 on diameter 8.8 mm that has asymmetric triangular profile, height 0.15 mm. The inner side of the barrier 20 is designed to shape the connecting surface 6 in FIG. 3A.

The part 18A has the shaping surface 19A that is divided into the central part 21 of diameter 7.1 mm and the peripheral part 22A of the diameter 13 mm. The peripheral part is formed by a hyperboloid with the central radius 3.25 mm and the conic constant −6.26. The peripheral hyperbolic surface is parallel to the corresponding surface of the part 18B. The central portion of the part 18A is a plane perpendicular to the optical axis 1A.

About 0.1 ml of the monomer mixture is pipetted into the part 18B, then it is covered by the part 18A that is carefully centered and pressed gently against it by a small weight. The only direct contact between the parts is the circular contact between the barrier 20 and the peripheral part of 22A. The mold is then heated to 75° C. for 6 hours.

The mold parts are separated and the xerogel lens, the exact copy of the mold cavity, is neutralized by solution of sodium bicarbonate and extracted 3 times with ethyl alcohol and 5 times with isotonic solution. The lens was yellow with complete absorption of UV light and part of the blue visible light. The linear expansion factor between the xerogel and hydrogel lens is 1.13. After evaluation of optical properties the lens was immersed in the 15% by weight aqueous solution of NaCl in a sealed blister package and sterilized by autoclaving.

Example 3

The following monomer mixture was prepared: 94.5 weight parts of 2-hydroxyethyl methacrylate (HEMA), 0.5 w.p. of triethyleneglycol dimethacrylate (TEGDMA), 5 w.p. of methacryloyloxybenzophenone (MOBP) and 0.25 w.p. of dibenzoylperoxide. The mixture was de-aired using nitrogen carbon and filled into two-part plastic molds shown schematically in FIG. 8. The shaping surface 19B of the part 18B has a shape formed by two concentric surfaces. The central part of the surface has the diameter 6.5 mm, central radius of 4.5 mm and conic constant 0 while the peripheral section is a hyperboloid with central radius of 4.25 mm and conic constant −8. The molding surface is equipped with a protruding circular barrier 20 on diameter 9.3 mm that has asymmetric triangular profile, height 0.35 mm. The inner side of the barrier 20 is designed to shape the connecting surface 6 in FIG. 3A.

The part 18A has the shaping surface 19A that is divided into the central part 21 of diameter 6.4 mm and the peripheral part 22A of the diameter 13 mm. The peripheral part is formed by a hyperboloid with the central radius 4.25 mm and the conic constant −8. The peripheral hyperbolic surface is parallel to the corresponding surface of the part 18B. The central portion of the part 18A is a surface of diameter 6.4 mm, central radius −3.75 mm and conic constant −6.

About 0.1 ml of the monomer mixture is pipetted into the part 18B, then it is covered by the part 18A that is carefully centered and pressed gently against it by a small weight. The only direct contact between the parts is the circular contact between the barrier 20 and the peripheral part of 22A. The mold is then heated to 75° C. for 6 hours.

The mold parts are separated and the xerogel lens, the exact copy of the mold cavity, is extracted. The lens is then treated by a quaternary base as described in the reference Stoy '208.

The z lens from the clear, electroneutral crosslinked hydrophilic polymer has a surface created by a gradiented layer with high hydration and negative charge density. The lens was neutralized by solution of sodium bicarbonate and extracted 3 times with ethyl alcohol and 5 times with isotonic solution. The lens was clear with complete absorption of UV light. The linear expansion factor between the xerogel and hydrogel lens is about 1.12. After evaluation of optical properties the lens was immersed in the isotonic aqueous solution of NaCl in a sealed blister package and sterilized by autoclaving.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. An artificial lens implant implantable into the posterior chamber of a human eye for replacement of a natural crystalline lens, the implant comprising:
a body defining a central optical part and an integral peripheral supporting part, both of which extend about a main optical axis, wherein the central optical part has a refractive power;
the central optical part having a central anterior optical surface within a first boundary and defining an anterior apex, and a central posterior optical surface within a second boundary and defining a posterior apex, wherein the central anterior optical surface has a refractive power, wherein the central posterior optical surface has a refractive power and wherein the central posterior optical surface faces toward the posterior of the eye when implanted into the posterior chamber of the eye;
the peripheral supporting part having an anterior peripheral supporting surface extending from the first boundary such that the central anterior optical surface and the anterior peripheral supporting surface define an anterior surface with a first upper boundary, and a posterior peripheral supporting surface extending from the secondary boundary such that the central posterior optical surface and the posterior peripheral supporting surface define a posterior surface with a second upper boundary, and wherein the first upper boundary is anterior to the anterior apex of the central anterior optical surface;
a transition surface extending between the first upper boundary and the second upper boundary;
wherein at least the posterior surface has a convex shape and is made from a transparent flexible hydrogel material containing negatively charged ionizable functional groups selected from the group consisting of carboxyl group, sulpho-group, sulphate group, and phosphate group, in average concentration from about 0.15 molar % to about 5 molar %; wherein said hydrogel has an equilibrium intraocular fluid content between about 35 weight % and about 55 weight % of liquid;
wherein at least the central anterior optical surface and the central posterior optical surface are defined by rotation of one or more conic sections along the main optical axis and the surfaces defined by the rotation of the one or more conic sections include a plane perpendicular to the axis and a conical surface symmetrical about the axis; and
wherein the refractive power of the central optical part decreases from a highest value at the main optical axis to a lowest value at a periphery of the central optical part.

2. The artificial lens according to claim 1 wherein the transition surface is limited by at least one circumferential rim with a sharp edge.

3. The artificial lens according to claim 1 wherein the anterior apex does not extend beyond a further extending one of the first upper boundary and the second upper boundary.

4. The artificial lens according to claim 1 wherein the one or more conic sections is a hyperbola or a parabola.

5. The artificial lens according to claim 1 wherein the anterior peripheral supporting surface and the posterior peripheral supporting surface are coaxial hyperbolic or conical surfaces.

6. The artificial lens according to claim 1 wherein the convex posterior surface is symmetrical along the main optical axis and the posterior apex is located on the main optical axis.

7. The artificial lens according to claim 6 wherein the convex posterior surface comprises a hyperboloid surface symmetrical along the main optical axis.

8. The artificial lens according to claim 6 wherein the central posterior optical surface is a hyperboloid surface symmetrical along the main optical axis.

9. The artificial lens according to claim 1 wherein the posterior peripheral supporting surface is a hyperboloid surface or a cone surface symmetrical along the main optical axis.

10. The artificial lens according to claim 1 wherein the convex posterior surface is formed by two or more different coaxial hyperbolic surfaces.

11. The artificial lens according to claim 1 wherein the central optical anterior surface is a plane, a convex surface or a concave surface with the anterior apex not extending more than 0.25 mm beyond a further extending one of the first upper boundary and the second upper boundary.

12. The artificial lens according to claim 11 wherein the central optical anterior surface is a hyperboloid surface symmetrical to the main optical axis, a spherical surface symmetrical to the main optical axis, a parabolic surface symmetrical to the main optical axis, or a plane perpendicular to the main optical axis.

13. The artificial lens according to claim 1 wherein a distance between the anterior apex and the posterior apex is not larger than a sagittal depth of the posterior surface, defined as a distance between a plane of the second upper boundary and the posterior apex.

14. The artificial lens according to claim 1 wherein at least one of the central anterior optical surface or the central posterior optical surface is configured to approximate a hyperbolic surface shape of a natural healthy young human lens.

15. The artificial lens according to claim 14 wherein both the central anterior optical surface and the central posterior optical surface are configured to approximate the hyperbolic surface shape of the natural healthy young human lens.

16. The artificial lens according to claim 1 wherein at least one of the central anterior optical surface or the central posterior optical surface is formed by two or more concentric surfaces formed by rotation of different conic sections along the main optical axis.

17. The artificial lens according to claim 16 wherein the concentric surfaces are different hyperbolic surfaces.

18. The artificial lens according to claim 1 wherein both the first and the second boundaries are circular in a plane perpendicular to the main optical axis.

19. The artificial lens according to claim 1 wherein the first upper boundary and the second upper boundary define an anterior rim and a posterior rim, respectively, and the anterior rim and the posterior rim each have a non-circular shape in a plane perpendicular to the main optical axis.

20. The artificial lens according to claim 19 wherein at least one of the non-circular shapes is the shape of a truncated circle, a double truncated circle, or a triple truncated circle.

21. The artificial lens according to claim 1 wherein the hydrogel has a gradient of concentration of the ionizable functional groups where a highest concentration is on the surface of the hydrogel.

22. The artificial lens according to claim 1 wherein at least the central optical part comprises at least two transparent materials having different refractive indices.

23. The artificial lens according to claim 1 wherein the one or more conic sections are described by an equation $Y-Y_o = X^2 / \{R_o * (1+(1-h*(X/R_o)^2)^{0.5})\}$ wherein Y is a coordinate in a direction of the main optical axis, X is a distance from the main optical axis, Yo is an apex position on the main optical axis, Ro is a central radius of curvature and h is a conic constant of a conic curve.

\* \* \* \* \*